US009974619B2

(12) United States Patent
Goldenberg et al.

(10) Patent No.: US 9,974,619 B2
(45) Date of Patent: May 22, 2018

(54) SURGICAL ROBOT

(71) Applicants: Andrew A. Goldenberg, Toronto (CA); Yi Yang, Toronto (CA); Liang Ma, Markham (CA); Joao Guilherme Amaral, Toronto (CA); James Drake, Toronto (CA); Thomas Looi, Markham (CA)

(72) Inventors: Andrew A. Goldenberg, Toronto (CA); Yi Yang, Toronto (CA); Liang Ma, Markham (CA); Joao Guilherme Amaral, Toronto (CA); James Drake, Toronto (CA); Thomas Looi, Markham (CA)

(73) Assignees: ENGINEERING SERVICES INC., Markham (CA); THE HOSPITAL FOR SICK CHILDREN, Toronto (CA)

( * ) Notice: Subject to any disclaimer, the term of this patent is extended or adjusted under 35 U.S.C. 154(b) by 0 days. days.

(21) Appl. No.: 14/619,978

(22) Filed: Feb. 11, 2015

(65) Prior Publication Data
US 2016/0228189 A1 Aug. 11, 2016

(51) Int. Cl.
*A61B 19/00* (2006.01)
*A61B 34/30* (2016.01)
(Continued)

(52) U.S. Cl.
CPC .... *A61B 34/30* (2016.02); *A61B 2017/00477* (2013.01); *A61B 2017/00911* (2013.01);
(Continued)

(58) Field of Classification Search
CPC ............... A61B 19/22; A61B 19/2203; A61B 2019/2207; A61B 2019/2211;
(Continued)

(56) References Cited

U.S. PATENT DOCUMENTS

| 4,501,414 A | 2/1985 | Mason et al. |
| 4,888,555 A | 12/1989 | Vaughan et al. |

(Continued)

FOREIGN PATENT DOCUMENTS

| DE | 10030507 | 1/2002 |
| DE | 102013002831 | 8/2014 |

(Continued)

OTHER PUBLICATIONS

Camacho et al., Nonsusceptibility Artifacts Due to Metallic Objects in MR Imaging, JMRI, vol. 5, No. 1, Jan./Feb. 1995, pp. 75-88.
(Continued)

*Primary Examiner* — Shaun L David

(57) ABSTRACT

A modular reconfigurable surgical robot for use in association with a surgical tool is disclosed. The surgical robot includes a linear module for linear movement; a turret module for rotational movement, and elbow roll module for rotational movement, and a wrist tilt module for rotational movement. The turret module has a turret rotational axis. The elbow roll module for rotational has an elbow roll rotational axis at an angle to the turret rotational axis. The wrist tilt module has a wrist tilt rotational axis at an angle to the turret rotational axis and the elbow roll rotational axis. The linear module, turret module, elbow roll module and wrist tilt module are operably connectable together to form the surgical robot and one of the modules is operably connectable to the surgical tool. The surgical robot may include an arch device unit attachable to one of the other modules.

38 Claims, 23 Drawing Sheets

(51) Int. Cl.
  *A61B 17/00* (2006.01)
  *A61B 17/34* (2006.01)
  *A61B 90/00* (2016.01)

(52) U.S. Cl.
  CPC . *A61B 2017/3409* (2013.01); *A61B 2034/304* (2016.02); *A61B 2034/305* (2016.02); *A61B 2090/374* (2016.02)

(58) Field of Classification Search
  CPC .... A61B 2019/2215; A61B 2019/2219; A61B 2019/2223; A61B 2019/2226; A61B 2019/223; A61B 2019/2234; A61B 2019/2238; A61B 2019/2249; A61B 2019/2253; A61B 2019/2257; A61B 2019/2261; A61B 2019/2265; A61B 2034/301–2034/306; A61B 34/30
  See application file for complete search history.

(56) References Cited

U.S. PATENT DOCUMENTS

| | | | |
|---|---|---|---|
| 4,922,915 | A | 5/1990 | Arnold et al. |
| 4,923,459 | A | 5/1990 | Nambu |
| 5,071,602 | A | 12/1991 | Nambu et al. |
| 5,312,755 | A | 5/1994 | Madsen et al. |
| 6,318,146 | B1 | 11/2001 | Madsen et al. |
| 6,665,554 | B1 | 12/2003 | Charles et al. |
| 6,675,035 | B1 | 1/2004 | Grable et al. |
| D569,977 | S | 5/2008 | Luginbuhl et al. |
| 7,955,321 | B2 | 6/2011 | Kishi et al. |
| 8,275,443 | B2 | 9/2012 | Goldenberg et al. |
| 8,280,485 | B2 | 10/2012 | Goldenberg et al. |
| 8,491,603 | B2 | 7/2013 | Yeung et al. |
| 2001/0041838 | A1 | 11/2001 | Holupka et al. |
| 2003/0055436 | A1 | 3/2003 | Daum et al. |
| 2003/0065310 | A1 | 4/2003 | Wang et al. |
| 2003/0181807 | A1 | 9/2003 | Murphy et al. |
| 2004/0024385 | A1* | 2/2004 | Stuart .............. A61B 19/22 606/1 |
| 2005/0211905 | A1 | 9/2005 | Stark |
| 2007/0039101 | A1 | 2/2007 | Luginbuhl et al. |
| 2007/0088340 | A1 | 4/2007 | Brock et al. |
| 2007/0089557 | A1 | 4/2007 | Solomon et al. |
| 2007/0230757 | A1 | 10/2007 | Trachtenberg et al. |
| 2007/0262774 | A1 | 11/2007 | Schilling |
| 2008/0004481 | A1 | 1/2008 | Bax et al. |
| 2008/0255461 | A1 | 10/2008 | Weersink et al. |
| 2009/0163929 | A1* | 6/2009 | Yeung ............. A61B 19/2203 606/130 |
| 2009/0171185 | A1* | 7/2009 | Chou .................. 600/411 |
| 2009/0326365 | A1 | 12/2009 | Goldenberg et al. |
| 2010/0125192 | A1 | 5/2010 | Chopra et al. |
| 2010/0286669 | A1 | 11/2010 | Greer et al. |
| 2011/0118709 | A1* | 5/2011 | Burbank ........... A61B 19/2203 606/1 |
| 2012/0158017 | A1 | 6/2012 | Naylor et al. |
| 2014/0249546 | A1 | 9/2014 | Shvartsberg et al. |

FOREIGN PATENT DOCUMENTS

| | | |
|---|---|---|
| EP | 0919203 | 6/1999 |
| EP | 0922438 | 6/1999 |
| EP | 1103229 | 5/2001 |
| EP | 1815950 | 8/2007 |
| EP | 1839599 | 10/2007 |
| FR | 2576510 | 8/1986 |
| JP | 9266892 | 10/1997 |
| JP | 10057336 | 3/1998 |
| JP | 2006191939 | 7/2006 |
| JP | 2009539509 | 11/2009 |
| JP | 2009285099 | 12/2009 |
| WO | 95/16396 | 6/1995 |
| WO | 9520923 | 10/1995 |
| WO | 99/37220 | 7/1999 |
| WO | 00/49960 | 8/2000 |
| WO | 2004/019799 | 3/2004 |
| WO | 2004/029881 | 4/2004 |
| WO | 2004/080529 | 9/2004 |
| WO | 2005/046753 | 5/2005 |
| WO | 2005/092197 | 10/2005 |
| WO | 2006/089426 | 8/2006 |
| WO | 2007/065013 | 6/2007 |
| WO | 2007/106558 | 9/2007 |
| WO | 2007/106877 | 9/2007 |
| WO | 2008/031077 | 3/2008 |
| WO | 2008/042423 | 4/2008 |
| WO | 2008/059263 | 5/2008 |

OTHER PUBLICATIONS

Chopra et al, MRI-compatible transurethral ultrasound system for the treatment of localized prostate cancer using rotational control, Med Phys. 35(4)Apr. 2008, pp. 1346-1357.

Chopra et al. An MRI-compatible system for focused ultrasound experiments in small animal models. Phys. Med. 36 May 5, 2009, pp. 1867-1874.

* cited by examiner

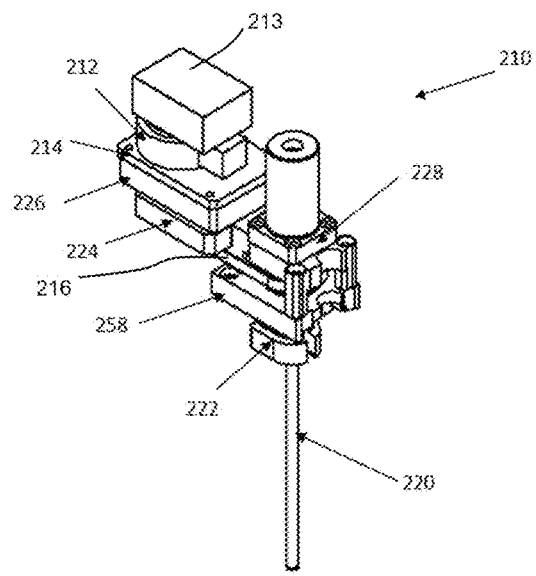
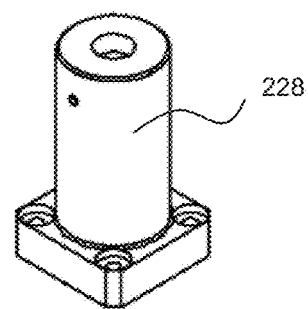
FIG. 14A  FIG. 14B
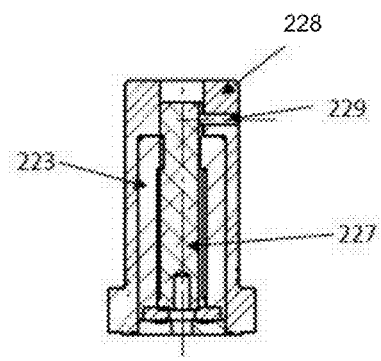
FIG. 14C

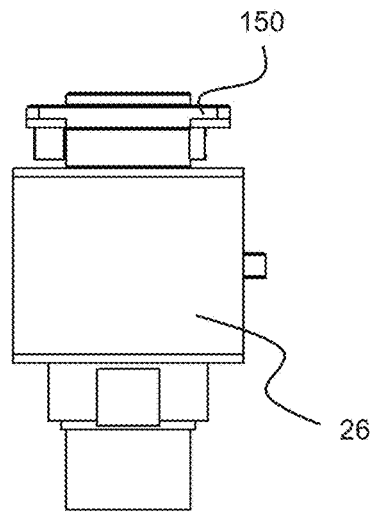
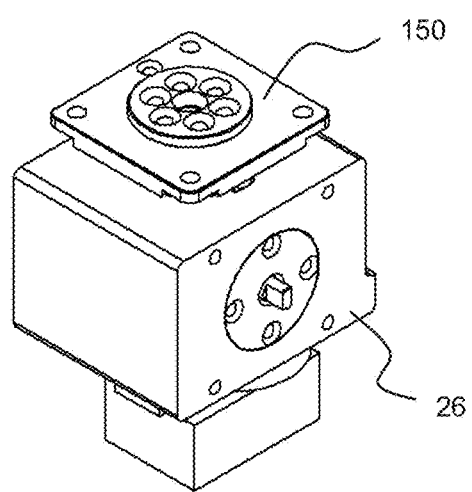
FIG. 29A                FIG. 29B
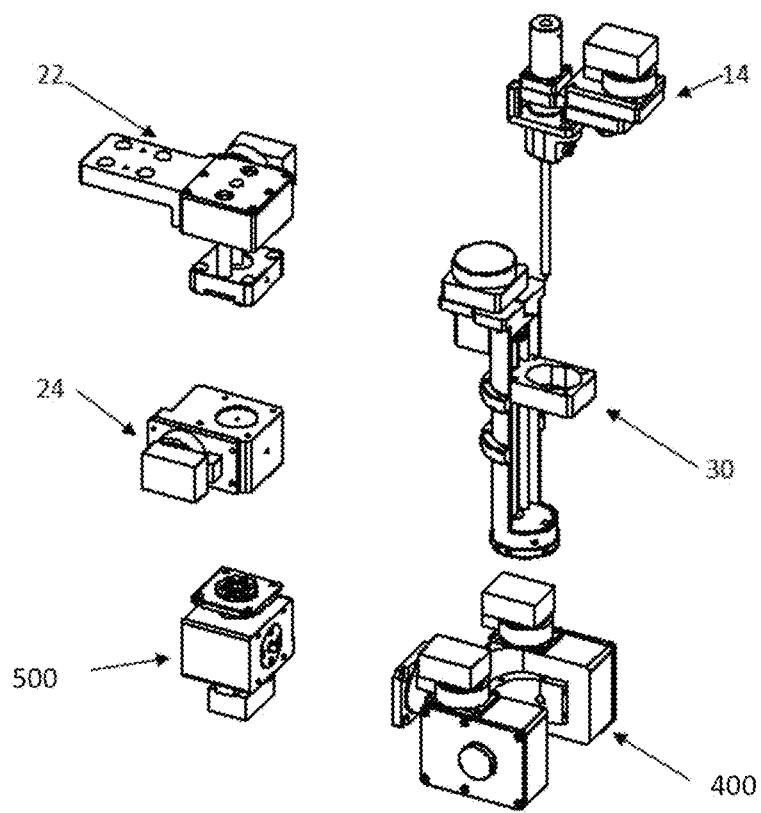
FIG. 30

SURGICAL ROBOT

FIELD OF THE DISCLOSURE

This disclosure relates to surgical robots and in particular surgical robots for use inside a magnetic resonance imaging (MRI) device.

BACKGROUND

It is well known that medical resonance imaging (MRI) devices have excellent soft tissue resolution and generate minimal radiation hazard. Because of these advantages MRI—guided robotic-based minimally invasive surgery has become an important surgical tool.

There are a number of surgical robots currently in use but not all are compatible with an MRI. For example the Intuitive Surgical robot called the da Vinci™ is not compatible with an MRI. In contrast the Innomotion robot arm, the NeuroArm robot, and the MRI-P robot are all MRI-compatible. However, even those robots which are MR compatible, may not be able to be operated during scanning.

The main reasons that the robots have not been widely used in the MRI environment are MRI incompatibility, limitations of the real-time intra-operative imaging, space constraints, and lack of compatible modular surgical tools.

SUMMARY

A modular reconfigurable surgical robot for use in association with a surgical tool is disclosed. The surgical robot includes a linear module for linear movement; a turret module for rotational movement, and elbow roll module for rotational movement, and a wrist tilt module for rotational movement. The turret module has a turret rotational axis. The elbow roll module for rotational has an elbow roll rotational axis at an angle to the turret rotational axis. The wrist tilt module has a wrist tilt rotational axis at an angle to the turret rotational axis and at an angle to the elbow roll rotational axis. The linear module, turret module, elbow roll module and wrist tilt module are operably connectable together to form the surgical robot and one of the modules is operably connectable to the surgical tool.

The linear movement of the linear module may define a z axis. The turret rotational axis may be an axis parallel to the z axis. The elbow roll rotational axis may be around an x axis and the x axis may be generally orthogonal to the z axis. The wrist tilt rotational axis may be around a y axis and the y axis may be generally orthogonal to the z axis and transverse to the x axis.

The modular reconfigurable surgical robot may further include a penetration module connectable thereto and the surgical tool may be attachable to the penetration module.

The modular reconfigurable surgical robot may include a turret elbow connection module connectable to the turret module and the elbow roll module.

The modular reconfigurable surgical robot may include a roll connection unit connectable to the wrist tilt module and the elbow roll module.

The linear module may include a lead screw and nut and gear mechanism operably connected to a motor. The gear mechanism of the linear module may include a worm and worm gear and the motor may be an ultrasonic rotary motor.

The linear module may include a hard stop to limit movement of the nut.

The turret module may include a shaft and a gear mechanism operably connected to a motor. The gear mechanism of the turret module may include a worm and a worn gear and the motor of the turret module may be an ultrasonic rotary motor. The turret module may include a hard stop to limit the rotation of the shaft.

The elbow roll module may include a shaft and a gear mechanism operably connected to a motor. The gear mechanism of the elbow roll module may include a worm and a worm gear and the motor of the elbow roll module may be an ultrasonic rotary motor. The elbow roll module may include a hard stop to limit the rotation of the shaft.

The wrist tilt module may include a pair of shafts and a pair of gear mechanism operably connected to a pair of motor. Each gear mechanism of the wrist tilt module may include a worm and a worm gear and the motor of the wrist tilt module may be an ultrasonic rotary motor. The wrist tilt module may include a hard stop to limit the rotation of the shaft.

The penetration module may include a lead screw and nut and gear mechanism operably connected to a motor. The gear mechanism of the penetration module may include a pair of spur gears and the motor of the penetration module may be an ultrasonic rotary motor. The surgical tool may be a surgical tool module connectable to the penetration module and the surgical tool module may include a lead screw and nut and gear mechanism operably connected to a motor.

The surgical tool module may be operably connected to a drill kit. The surgical tool module further may include a timing belt and pulleys operably connect to the drill kit. The surgical tool module may include a pneumatic unit operably connected to the drill kit. The drill kit may include a trocar, a drill, and a guide stylet.

The penetration module may further include an adapter and the surgical tool module is attachable to the adapter. The adapter may include a nut portion, a removable front adapter portion connectable to the nut portion and a removable front closure portion connectable to the removable front adapter portion. The surgical tool kit may include a removable support releasably connectable to a slot plate. The removable front adapter portion, the removable front closure portion, the removable support and the drill kit are all sterilizable. The motor of the surgical tool module may be an ultrasonic rotary motor.

The modular reconfigurable surgical robot may include an arch device unit operably attachable to one of the linear module, the turret module, the elbow roll module and the wrist tilt module. The arch device unit may include a pair of linear actuators at either end of an arch frame. Each linear actuator of the arch device unit may include an ultrasonic motor operably connected to a lead screw and a pair of carriages moveably connected to the lead screw and whereby the pair of carriages may be connected to the arch frame and activating the ultrasonic motor moves the carriage along the lead screw. Each linear actuator may be connected to a base plate and the base plate may be connectable to a surgical table.

The modular reconfigurable surgical robot may include a quick connector module connectable to one of the linear module, the turret module, the elbow roll module and the wrist tilt module. The arch device unit may include a rail and the surgical robot may be movably attached to the rail. The surgical robot may be moved manually along the rail. The arch device unit may include an arch motor to driven surgical robot along the rail.

All of the elements of the modular reconfigurable surgical robot may be MRI compatible.

A surgical robot assembly for use in association with a surgical tool or a surgical tool module is disclosed. The surgical robot assembly includes an arch unit having an arch frame and a surgical robot moveably attachable to the arch unit at different locations along the arch frame.

The arch unit further may include a pair of linear actuators at either end of the arch frame. Each linear actuator may include an ultrasonic motor operably connected to a lead screw and a pair of carriages moveably connected to the lead screw and whereby the pair of carriages may be connected to the arch frame and activating the ultrasonic motor moves the pair of carriages along the lead screw. Each linear actuator may be connected to a base plate and the base plate may be connectable to a surgical table. The arch unit may include a rail and the surgical robot is movably attached to the rail. The surgical robot is moved manually along the rail. The arch device may include an arch motor to driven surgical robot along the rail.

A surgical robot for use in association with a tool kit is disclosed. The surgical robot includes at least one rotary motion assembly; and a penetration module operably connected to one of the rotary motion assembly. The penetration module may include an adapter having a nut portion, a removable front adapter portion connectable to the nut portion and a removable front closure portion connectable to the removable front adapter portion. The tool kit is attachable to the adapter.

The surgical tool kit may include a removable support releasably connectable to a slot plate. The removable front adapter portion, the removable front closure portion, the removable support and the tool kit may all be sterilizable.

Further features will be described or will become apparent in the course of the following detailed description.

BRIEF DESCRIPTION OF THE DRAWINGS

The embodiments will now be described by way of example only, with reference to the accompanying drawings, in which:

FIG. 14A is a perspective view of a surgical tool module for use with the surgical robot of FIG. 2;

FIG. 14B is a perspective view of the trocar locking and retracing unit of the surgical tool module of FIG. 14A;

FIG. 14C is a section view of the trocar locking and retracing unit of the surgical tool module of FIG. 14A;

FIG. 29A is a perspective view of a the elbow roll module of FIG. 5 connected to the turret and elbow connection unit of FIGS. 8 and 9;

FIG. 29B is a side view of the elbow roll module and elbow turret connection unit of FIG. 29A; and FIG. 30 is a blown apart view of an alternate embodiment of the surgical robot.

DETAILED DESCRIPTION

Figure 1:
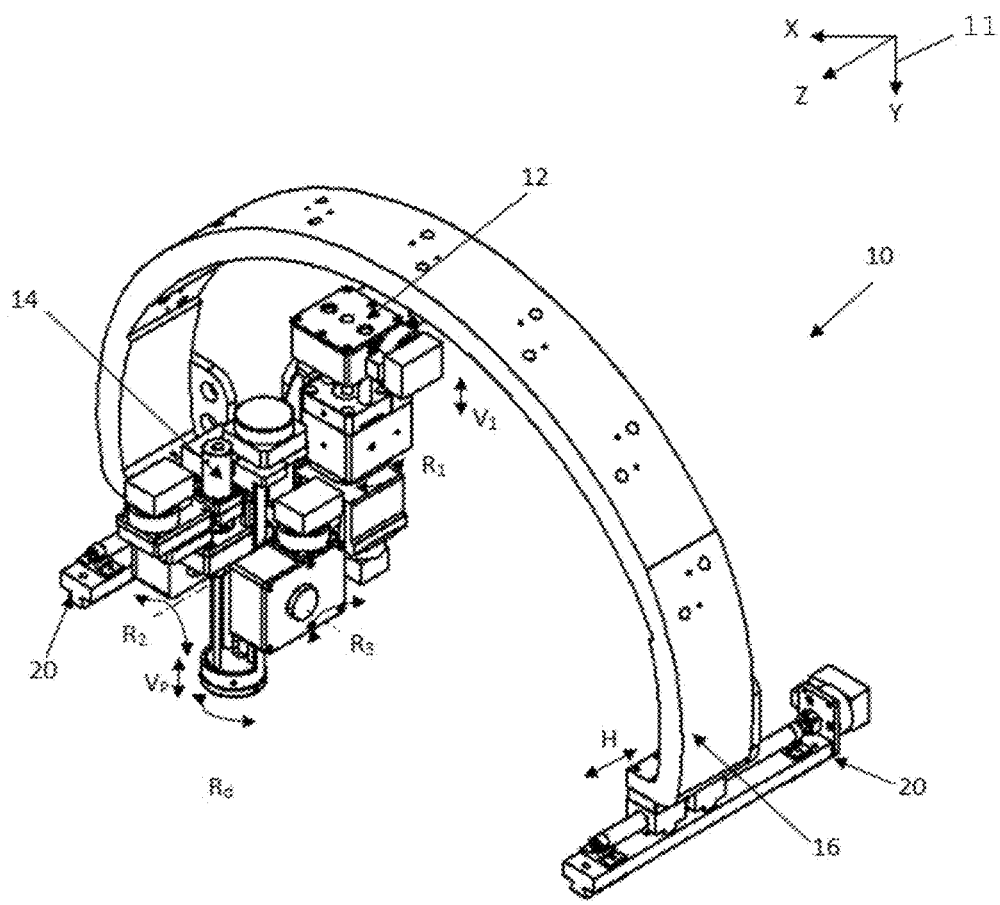
FIG. 1 is a perspective view of a surgical robot assembly adapted for use in an MRI.

Referring to FIG. 1, the surgical robot assembly adapted for use in an MRI (magnetic resonance imaging) device is shown generally at 10. The surgical robot assembly 10 includes a surgical robot 12, a surgical tool module 14, and an arch device unit 16. The surgical robot 12 is releasably attachable to the arch device unit 16 at different locations along the arch unit 16. The surgical tool module 14 is releasably attached to the surgical robot 12. The arch unit 16 includes a pair of rails 20 at each end thereof. The rails 20 are affixed or affixable to the MRI scanner roll-up table (not shown). Surgical robot assembly 10 is modular, reconfigurable and capable of fitting into an MRI environment. The re-configurability can provide a means of finding best possible configuration for specific procedures.

The surgical robot assembly 10 is MRI compatible and each component used therein is similarly MRI compatible. The surgical robot assembly 10 which includes a small surgical robot 12 is designed to fit within the specific space limitations of an MRI bore. The surgical robot 12 is mounted on an arched device unit 16. The surgical robot 12 includes self-contained modules that can be removed, exchanged and re-configured. The surgical tool module 14 includes a snap-on modular surgical tool an example of which is a tool for paediatric bone biopsy.

Where possible the components of the surgical robot 10 are made out of plastic. Preferably the plastic provides structural strength, is lightweight and is MR-compatible. By way of example the plastic is PEEK (Polyetheretherketone) material or Delrin® or SOMOS 11122xc or NEXT resin where rapid prototyping is used.

Figure 2A:
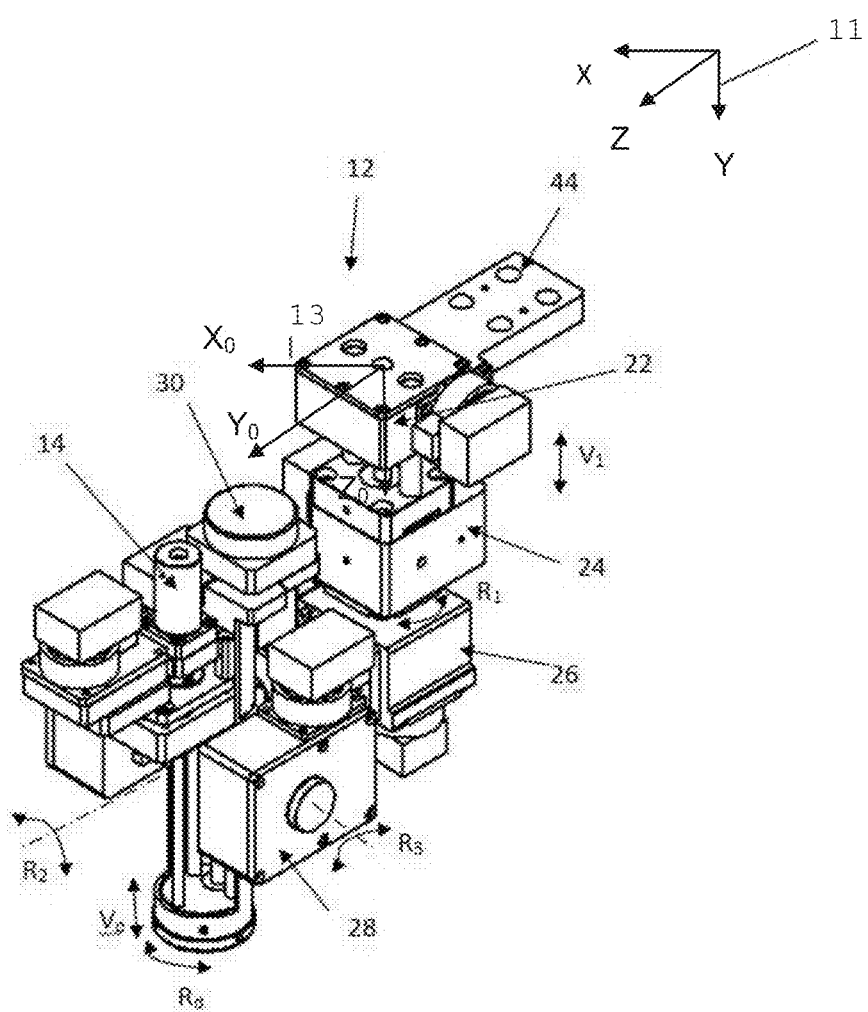
FIG. 2A is a perspective view of the surgical robot of the surgical robot assembly of FIG. 1.
Figure 2B:
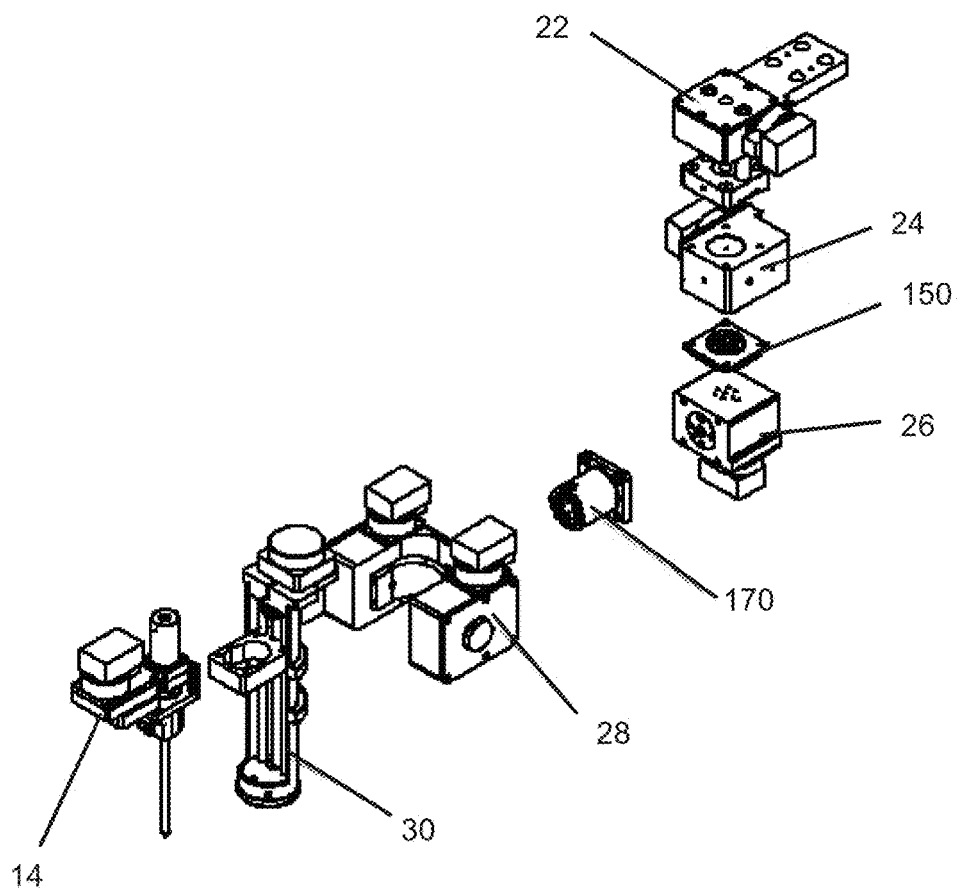
FIG. 2B is a blown apart perspective view of the surgical robot of FIG. 2*a;*

Referring to FIGS. 2A and 2B, the surgical robot 12, includes a linear motion assembly being a linear module 22, a first rotary motion assembly being a turret module 24, a second rotary motion assembly being an elbow roll module 26, a third rotary motion assembly being a wrist tilt module 28 and another linear motion assembly being a penetration module 30. The turret module 24 and the elbow roll module 26 are connected with a turret and elbow connection unit 150. The elbow roll module 26 and the wrist tilt module 28 are connected with the roll connection unit 170. Alternatively the elbow roll module could include a connector and similarly the wrist tilt module could include a connector and thereby the surgical robot would include a linear module, a turret module, an elbow roll module and a wrist module as described in more detail below with reference to FIG. 30

Figure 3A:
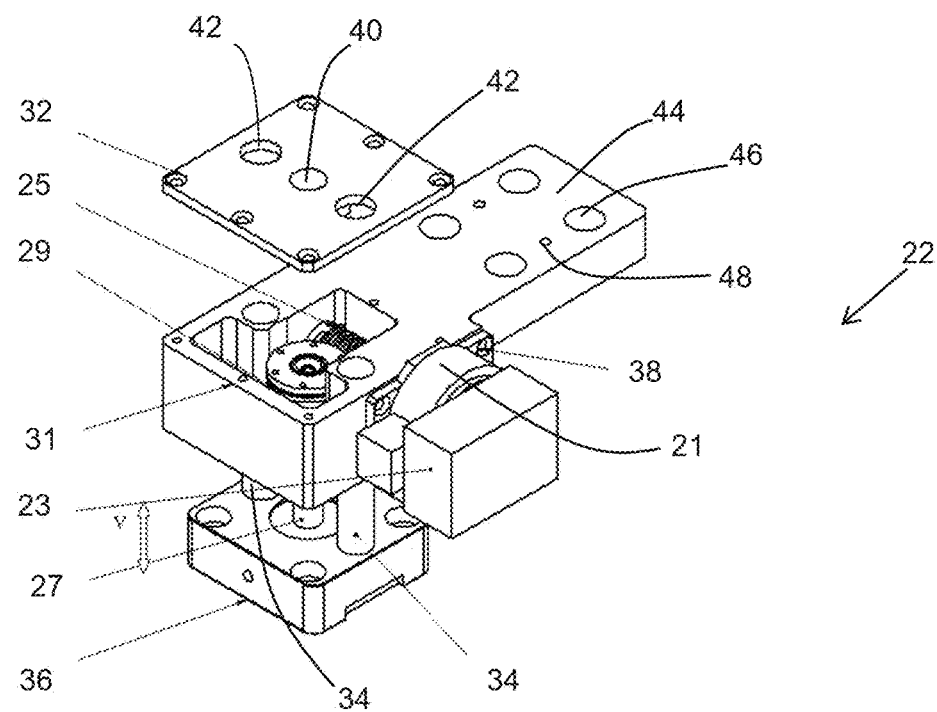
FIG. 3A is a perspective view of the vertical translation module of the surgical robot and showing the cover plate removed.
Figure 3B:
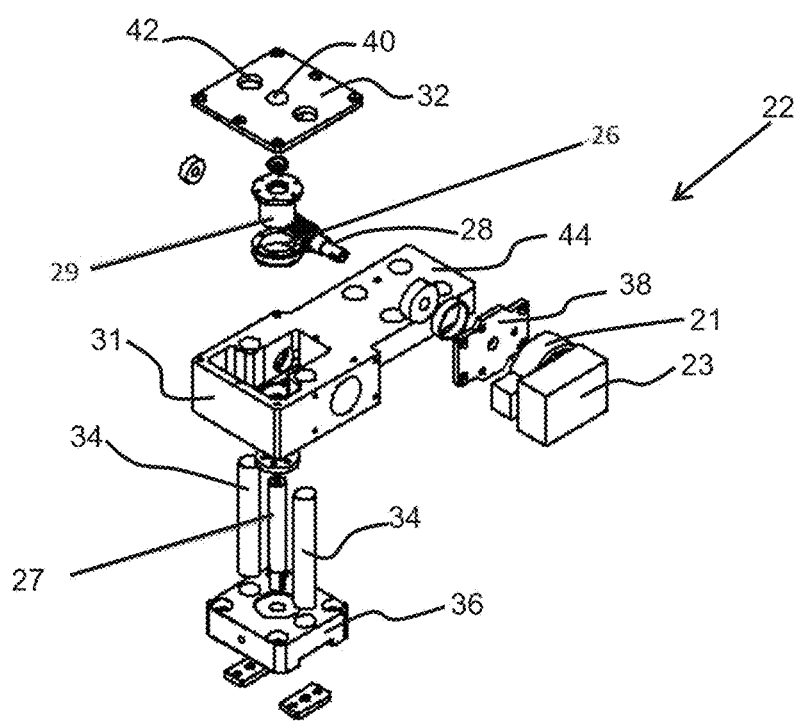
FIG. 3B is a blown apart perspective view of the translation module of FIG. 3A.

Referring to FIGS. 3A and 3B, the linear module 22 is a one degree of freedom joint. In the configuration shown in FIGS. 1, 2 and 3 it is provides for vertical translation or translation in the y axis. However, it will be appreciated that as the surgical robot moves around the arch device unit 16 the orientation of the linear module 22 will change and it will generally provide movement along a radius of the arch. The linear module includes an ultrasonic motor 21 with an encoder 23, a gear mechanism 25, a lead screw 27, a nut 29 and a support plate 36. In addition, the linear module 22 also includes a housing 31, a housing cover 32, a motor plate 38 and a pair of linear guide shafts 34. In addition, bearings are used as needed. Preferably the ultrasonic motor 21 is a combined ultrasonic rotary motor and encoder. Alternatively an ultrasonic motor and a separate encoder could be used. By way of example, a USR30 E3N motor may be used. Preferably the gear 26 is a worm gear. The ultrasonic motor 21 is operably connected to the worm gear 26. The worm gear 26 engages the nut 29 and the nut 29 moves along the lead screw 27. The worm gear 26 is used to increase the torque of the motor. In addition, worm gears are preferred because of their self-locking feature and their gear ratio. The lead screw 27 is attached to the support plate 36. Thus when the ultrasonic motor 21 is activated it causes the support plate to move in a linear direction as determined by the position of the nut 29 along the lead screw 27. In the embodiment herein the linear motion stroke is 0-30 mm. The lead screw 27 and the pair of guide shafts 34 are attached to the support plate 36 and are moveable relative to the housing 31. Preferably an ACME or Trapezoidal lead screw is used and since the ACME or Trapezoidal lead screw 27 is not back-driveable, it is reverse self-locking. The housing cover 32 and the motor plate 38 each attach to the housing 31 and together enclose the worm gear 26 and nut 29. The housing cover 32 has a shaft hole 40 and a pair of guide holes 42 such that the lead screw 27 and linear guides 34 can move freely therethrough. The housing 31 includes a quick connect attachment portion 44.

The quick connect portion 44 includes screw holes 46 and alignment pin holes 48. The quick connect portion 44 is connectable to the arch device unit 16 by inserting alignment pins (not shown) into alignment pin holes 48 on the quick connect portion 44 and the arch support 16 and then connecting them with screws (not shown) through the screw holes 46. The quick connect attachment allows the user to easily connect the surgical robot 12 at various locations along the arch device 16 as shown in FIGS. 1 and 24 and 25.

Figure 4:
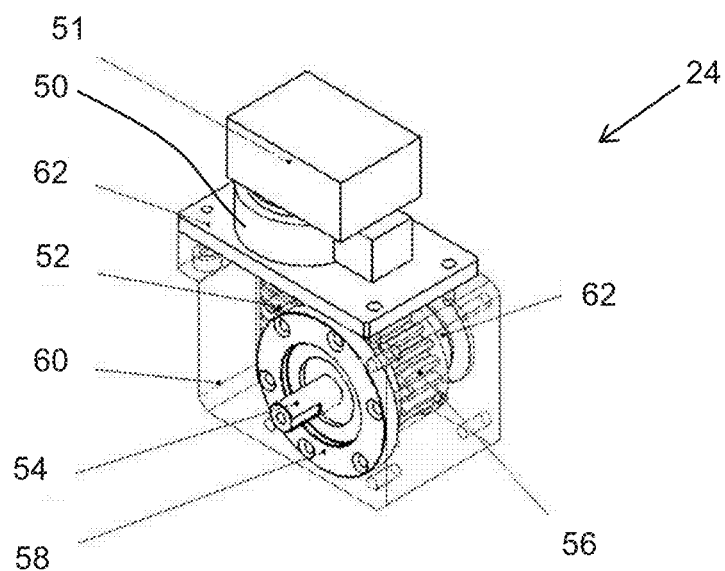
FIG. 4 is a perspective view of the turret module of the surgical robot of FIG. 2 and showing the turret housing as transparent.

The turret module 24 is shown in FIG. 4. The turret module 24 includes an ultrasonic motor 50, an encoder 51, a gear mechanism, a shaft 54, and a support plate 58. The turret module 24 also includes a housing 60 and a motor plate 62. Bearings are included where needed. Preferably the gear mechanism includes a worm 52 and a worm gear 56. Preferably the ultrasonic motor is a ultrasonic rotary motor and is a combined ultrasonic motor and optical encoder. By way of example a USR60-3EN or UST30-3EN ultrasonic rotary motor may be used. By way of example, the static torque rating of the worm gear 56 is 20 Nm. The cables (not shown), for the motor 50 and encoder, are outside the turret module 24. In the embodiment herein, the overall weight of the turret module is about 0.25 kg. The worm 52 and worm gear 56 provide a self-locking function. The self-locking function reduces the possibility of the output driving the input. Preferably the range of motion of the turret joint is −65 degrees to +65 degrees.

Figure 5:
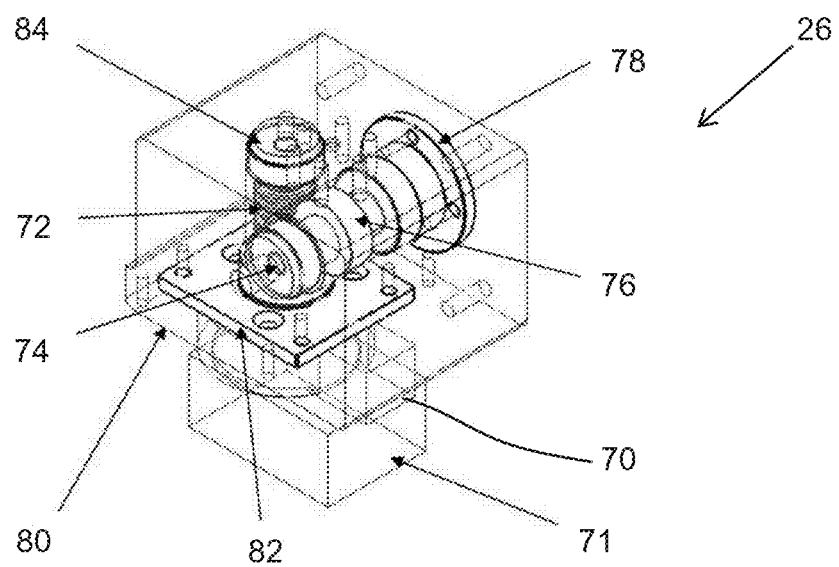
FIG. 5 is a perspective view of the elbow roll module of the surgical robot of FIG. 2 and showing the elbow roll housing as transparent.

Elbow roll module 26, shown in FIG. 5, has a structure that is somewhat similar to that of the turret module 24 described above. The elbow roll module 26 includes an ultrasonic motor 70, an encoder 71, a gear mechanism, a shaft 74, and a support plate 78. The elbow roll module 26 also includes a housing 80 and a motor plate 82. Bearings 84 are included where needed. Preferably, the gear mechanism includes a worm r 72 and a worm gear 76 operably connected to the shaft 74 to the ultrasonic motor 70. Preferably the ultrasonic motor is a USR ultrasonic rotary motor and is a combined ultrasonic motor and optical encoder. By way of example, the static torque rating of the worm gear 72 is about 4 Nm. Preferably the range of motion of the elbow roll joint is −70 degrees to +70 degrees.

Figure 6A:
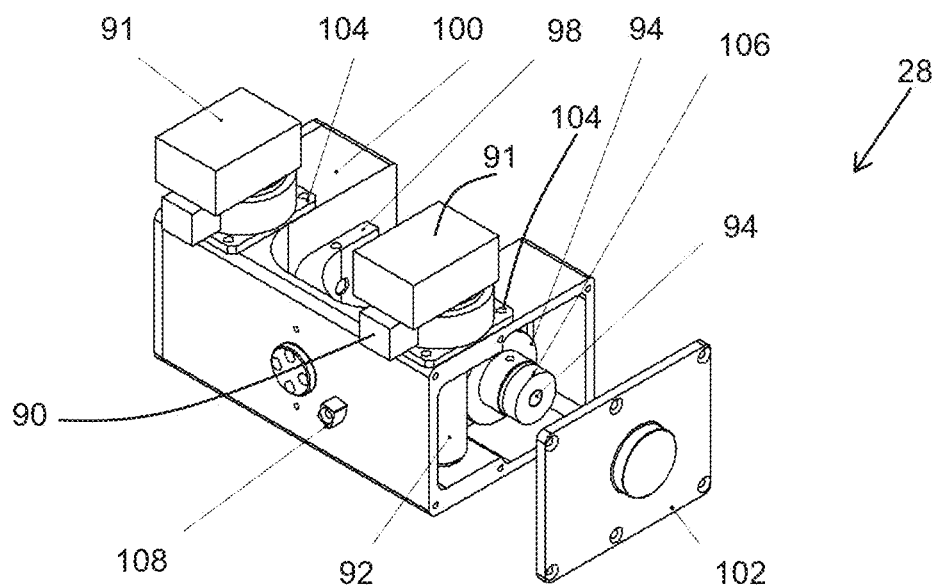
FIG. 6A is a perspective view of the wrist tilt module of the surgical robot of FIG. 2 and showing the cover plate removed.
Figure 12:
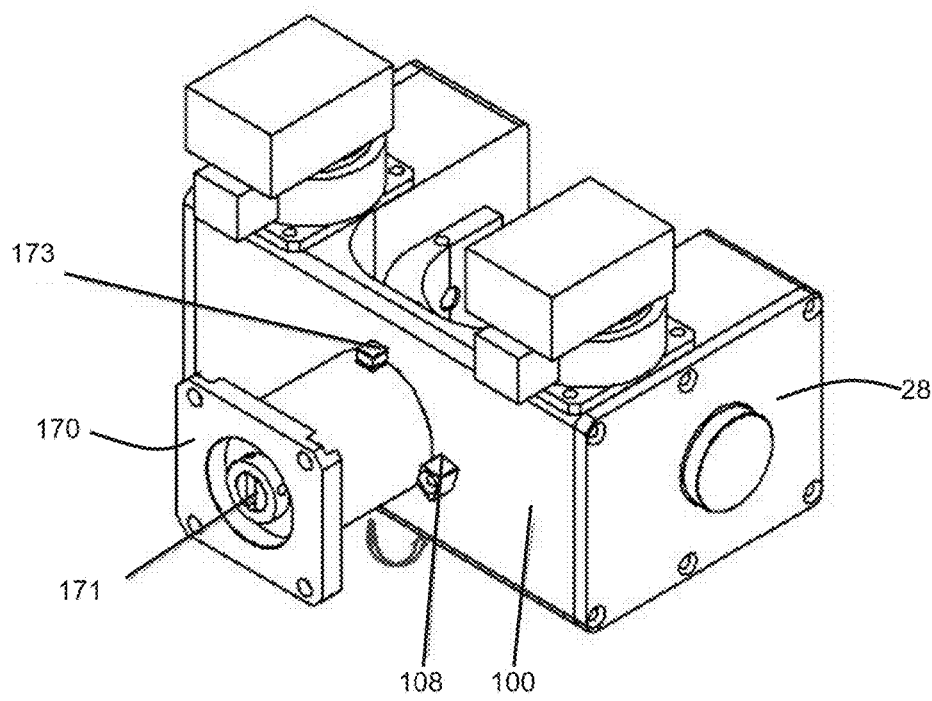
FIG. 12 is a perspective view of the wrist tilt module of FIG. 6 connected to the roll connection unit of FIGS. 10 and 11.

The wrist tilt module 28, shown in FIGS. 6A and B, is built with a symmetrical structure and includes a pair of ultrasonic motors 90, a pair of encoders 91, a pair of gear mechanisms, a pair of shafts 94, and a support plate 98. The wrist tilt module 28 also includes a housing 100, two housing covers 102 and two motor plates 104. Bearings 106 are included where needed. Preferably the ultrasonic motor is a USR ultrasonic rotary motor and is a combined ultrasonic motor and optical encoder. Preferably, the gear mechanism includes a worm 72 and a worm gear 96. Hard stop 105 and hard stop 107 limit the rotation angle of the support plate 98 which are fixed to the shafts 94 and rotate with the shafts 94. A hard stop 108 engages hard stop 173 on the roll connection unit 170 as shown in FIG. 12. Ultrasonic motors 90 work in parallel as the driving mechanisms to get the required rotating and stalling torque. By way of example, the static torque rating of the worm gears is about 15×2 Nm. Preferably the range of motion of the wrist tilt joint is −20 degrees to +20 degrees.

Figure 7:
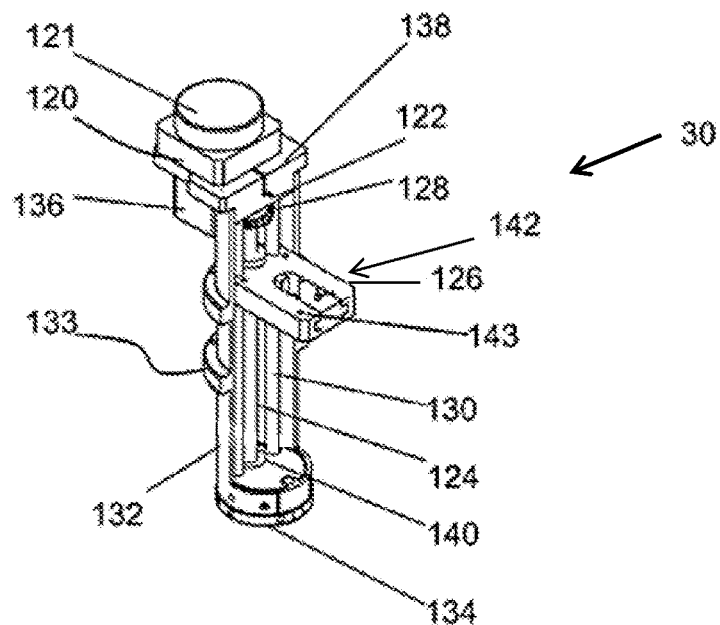
FIG. 7 is a perspective view of the penetration module of the surgical robot of FIG. 2.

The penetration module 30, shown in FIG. 7, includes an ultrasonic motor 120, an encoder 121, a force sensor 122, a lead screw 124, a nut 126 and gears 128. In addition, the penetration module 30 includes a pair of guide shafts 130, a swivel block 132 and a front support part 134. The swivel block 132 supports the lead screw 124 and the other parts of the linear mechanism. The swivel block 132 includes connection ribs 133 which are connected to the support plate 98 of the wrist tilt module 28. As well the penetration module 30 includes a housing 136 and motor plate 138. Bearings 140 are included where needed. Preferably the ultrasonic motor is a combined ultrasonic rotary motor and encoder. The nut 126 is adapted to be connectable to a surgical tool. In the embodiment shown in FIG. 7 the nut 126 includes an adapter portion 142 adapted to receive a surgical tool. The adapter portion 142 includes a plurality of threaded holes 143. The motor 120 is operably connected to a pair of gears 128, which are operably connected to the lead screw 124. Thus when the motor 120 is activated the gears 128 cause the lead screw 124 to rotate thus causing the nut 126 to moves linearly along the lead screw 124. The movement of the nut 126 produces thrust. By way of example the force sensor 122 is a FlexiForce A201 force sensor. The force sensor 122 is used to measure the penetration and drilling force. The FlexiForce A201 sensor is an ultra-thin flexible printed circuit that is integrated into the penetration module. The force sensor 122 allows for haptic control of the surgical robot 12. Preferably the range of motion of the penetration joint is 0-90 mm.

Figures 8, 9:
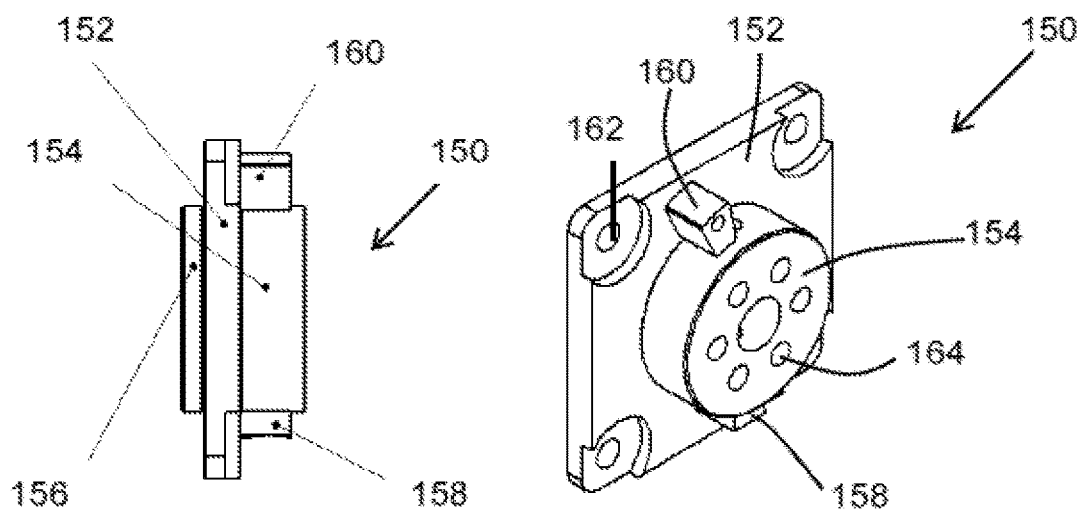
FIG. 8 is a side view of the turret and elbow connection unit of the surgical robot of FIG. 2.
FIG. 9 is a perspective view of the turret and elbow connection unit of FIG. 7.

A turret and elbow connection unit 150 is shown in FIGS. 8 and 9. This unit connects the turret module 24 and elbow roll module 26 and is a slewing bearing. FIGS. 29A and 29B show elbow roll module 26 connected to turret and elbow connection unit 150. Unit 150 includes a support plate 152 with a first slewing ring 154 on one side thereof and a second slewing ring 156 on the other side thereof. A first hard stop 158 is attached on first slewing ring 154 and a second hard stop 160 is attached to the support plate 152. The support plate 152 is provided with plurality of apertures 162 and the turret module 24 is attached thereto. The first slewing ring 154 is provided with a plurality of apertures 164 and the elbow role module 26 is attached thereto. The slewing bearing uses self-lubricating, low-friction sliding elements in place of ball bearings. Preferably these are made from low-cost, high-performance plastic called Iglide J™ material, which is designed to be lubrication and maintenance-free. The support plate 152 is made of PEEK (Polyetheretherketone) material. The turret and elbow connection unit 150 is designed to be low profile, low weight, lubrication-free and easy to install. Alternatively an alternate elbow roll module 500 may combine the features of the elbow roll module of FIG. 5 and the features of the turret and elbow connection unit of FIGS. 8 and 9, as shown in FIG. 30.

Figure 6B:
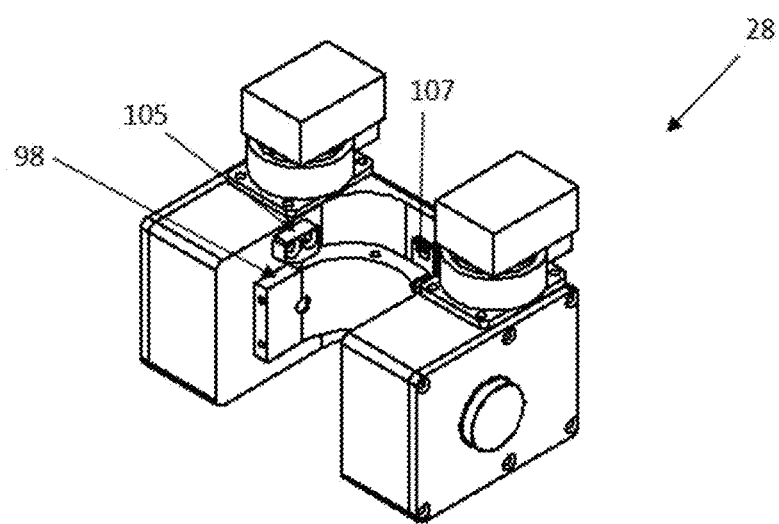
FIG. 6B is a perspective view of the wrist tilt module of FIG. 6A but viewed from a different angle.
Figure 10:
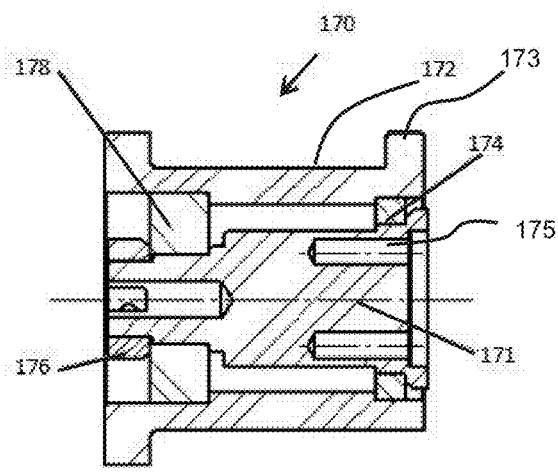
FIG. 10 is a cross sectional view of the roll connection unit of the surgical robot of FIG. 2.
Figure 11:
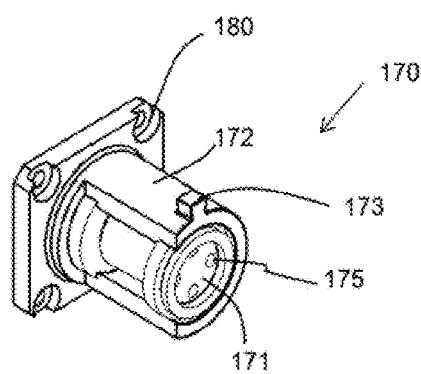
FIG. 11 is a perspective view of the roll connection unit of FIG. 10 with a portion of the housing broken away.

The elbow roll module 26 and the wrist tilt module 28 are connected with the roll connection unit 170 that is shown in FIGS. 10 and 11. The roll connection unit 170 consists of a support part or housing 172, shaft 171, bearings 174 and a shaft ring 176. The housing 172 includes a hard stop 173. The shaft ring 176 includes a plurality of apertures 178 and the elbow module 26 is connected thereto. The shaft 171 has a plurality of apertures 175 and the wrist tilt module 28 is connected thereto as shown in FIG. 12. Alternatively an alternate wrist tilt module 400 may combine the features of wrist tilt module of FIG. 6 and the features of the roll connection unit of FIGS. 10 and 11, as shown in FIG. 30.

Figure 13:
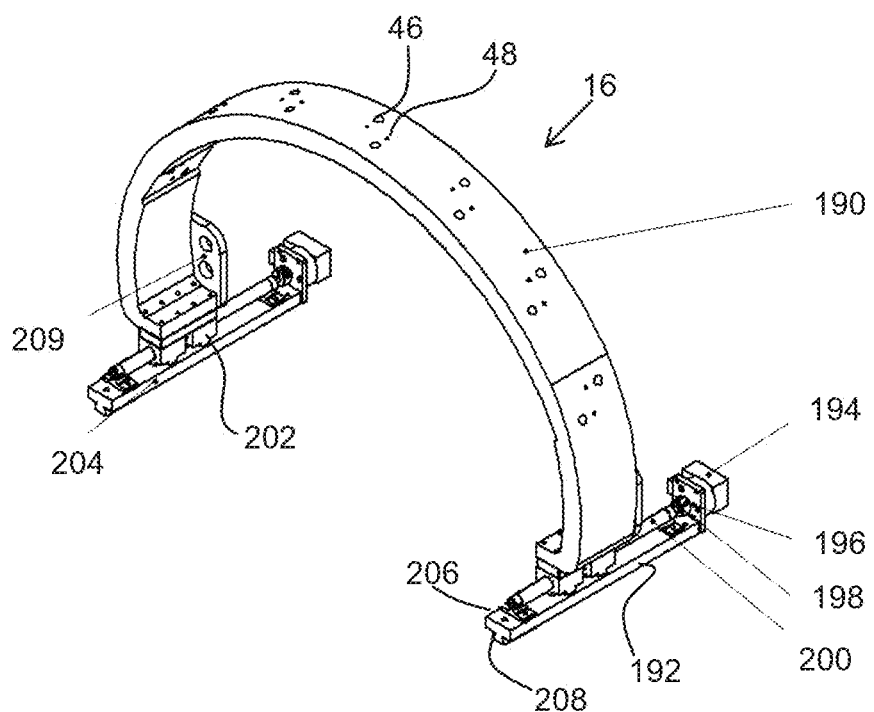
FIG. 13 is a perspective view of the arch device unit of the surgical robot assembly of FIG. 1.

The arch unit 16 is shown in FIG. 13. The arch unit 16 includes an arch frame 190 that is moveable along a pair of linear actuators 192 connected at each end thereof. Each linear actuator 192 includes an ultrasonic motor 194, an encoder 195, a motor plate 196, collar 198 and a lead screw 200. Preferably the ultrasonic motor 194 and encoder 195 are a combined ultrasonic rotary motor and encoder. A pair of carriages 202 is moveably attached to the lead screw 200 and integrally formed in the arch frame 190. Bearings are included where needed. Each linear actuator 192 is connected to a base plate 204 which is connectable to an MRI table 206 (shown). In the embodiment shown herein the base plate 204 has a central ridge 208 extending downwardly from the centre thereof. The ridge is adapted to engage a slot in the MRI table. A thumb screw (not shown) may be used for locking the base plates 204 in place. The arch 190 is provided with a cable connector plate 209. (Note, the cables are not shown in the drawings so as to simplify the drawings.) The linear actuators 192 control the position of the arch frame 190 along the linear axis of the lead screws 200 or base plates 204. Since the base plates 204 are attached to the MRI table and the table 206 is insertable into the MRI, the motion of the arch frame 190 along the lead screws 200 will be along the longitudinal axis of the MRI scanner. Preferably, the stroke of the linear motion is 0-100 mm, however, this can be varied depending on the length of the MRI. The arch unit has two linear actuators that work in parallel and they slide the arch unit 16 along the longitudinal axis of the scanner.

In the embodiment shown in FIGS. 1 to 13, the surgical robot 12 is positioned along the arch unit 16 with a quick—connect attachment and alignment pins. Quick connect attachments and alignment pins 46 are located on the quick connect portion 44 of the linear module 22 which provides for the connection of the surgical robot 12 to the arch frame 190. The positioning on the arch frame 190 and modules-based re-configurability of the surgical robot 12 provide the means of finding optimal locations and poses for specific surgical tasks.

Preferably the actuators or motors are ultrasonic motors that are retentive. Preferably the gears are self-locking worm mechanisms or non-back-drivable lead screws in order to lock the joints of the surgical robot assembly 10 and the surgical tool into position without brakes.

The hard stop 108 engages the hard stop 173 on roll connection unit 170 and is used to stop the shaft 94 of the wrist tilt module 28 rotating when the rotation joint reaches the hard limit by absorbing the force of the impact. In addition hard stops 158 and 160 are provided on the turret and elbow connector unit 150. Since the hard stops are used, electronic sensors and their cables need not be used to define the hard limit of the motors. The linear motion module 22 uses the housing cover 32 and the plate support 36 form the homing procedure described below. The advantage of using a mechanical stop rather than electronic sensors is that electronic sensors may distort the MR imaging and be affected by the MR scanning. In use, when the motor is moving, a controller keeps track of the encoder reading as a feedback of motor position. If during a predetermined period of time, the encoder reading does not change, it is deduced that the motor has hit the hard stop. Then the controller will send a "stop" command to the motor to stop the motion. Thereafter, only a motion command to the move in the opposite direction will be accepted.

The homing mode is used to reset the encoder counter at each boot up of the surgical robot assembly 10. More specifically, the homing function is for determining the position of each joint after power up. Without homing the controller will not know the current position of each joint after power up. The homing procedure includes the following steps: a) first move each joint in a known direction at known speed and b) once the joint reaches homing offset (a known location) the controller will then receive a signal from the sensor. The homing offset is a known position and it is the reference of home (zero) position of a joint. The homing offset and homing speed are defined for each joint. The homing offset allows setting the actual zero at a given distance from the hard stop. For safety, a lower speed is imposed when approaching the hard stop.

Preferably linear module 22, turret module 24, elbow roll module 26, wrist module 28 and penetration module use worm gears as their gears. The worm gears are high-ratio, non-back-drivable worm mechanisms. By way of example the worm gear for the turret module 24 is a 20 ratio gear; for the elbow roll module 26 is a 18 gear ratio; for the wrist tilt module 28 is a 24 gear ratio; and for the linear module 22 is a 12.5 gear ratio, The worm gears provide good load-carrying capabilities with relatively low-power actuators. By way of example the turret module 24, the elbow roll module 26, the wrist tilt module and the linear module 22 each have a 1.0 W actuator. The worm gears provide a compact means of substantially decreasing speed and increasing torque. Alternatively if spur gears were used the surgical robot would be larger. Further the worm gears are self-locking and are not back-drivable. When the lead angle of the worm is smaller than the friction angle of the meshing gear, worm mechanism generates the reverse self-locking. Thus, the worm can drive the worm wheel, but the worm wheel cannot drive the worm. The worm gear help to provide modules that are simpler and smaller in volume.

An embodiment of the surgical tool module is shown in FIG. 14 at 210. The surgical tool module 210 includes an ultrasonic motor 212, an encoder 213, a motor plate 214, a gear mechanism 226, a timing belt and a pair of pulleys 216, and a lead screw 227. Preferably the ultrasonic motor is an ultrasonic rotary motor and includes an encoder and more specifically an optical encoder. The surgical tool module 210 is for use with a drill kit 220. Preferably the drill kit 220 includes a sterile serrated hollow drill. The surgical tool module 210 includes a removable drill support 222 for supporting the drill kit 220. Removable drill support 222 is releasably connectable to slot plate 258. The surgical tool module 210 also includes a support frame 224 and a guide support 228. Guide support 228, best seen in FIGS. 14B and 14C includes a lead screw 227 with a nut 223. The lead screw can linearly move up and down along the guide support 228 by using a pin 229 that engages a slot on the lead screw 227. Bearings are included where needed. The ultrasonic motor 212 is operably connected to the timing belt and pulleys 216, which in turn are operably connected to the drill kit 220 to rotate the drill. The ultrasonic motor 212 is also operably connected to gears in the gear box 226 which are operably connected to the lead screw 227 through pulley 216. The cables for the motor 212 and encoder 213 are outside the module (not shown). It should be noted that in this embodiment the retracing mechanism and needle rotation are driven by one ultrasonic motor.

Figure 15A:
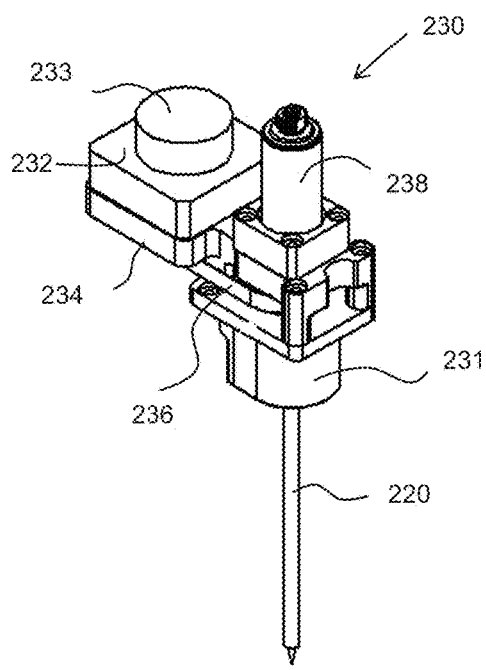
FIG. 15A is a perspective view of an alternate surgical tool module for use with surgical robot of FIG. 2.
Figure 15B:
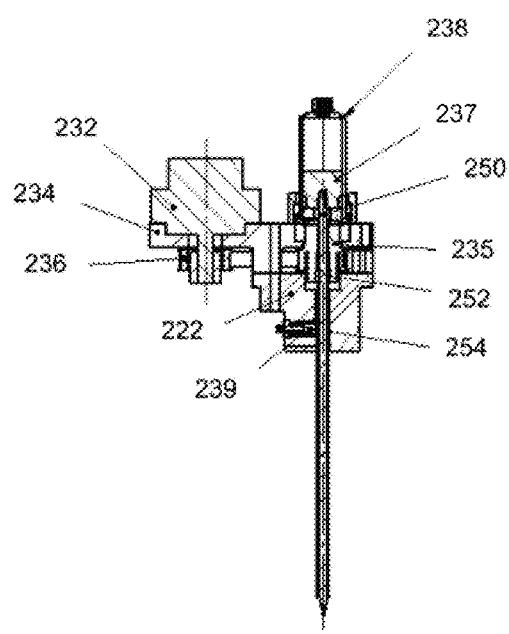
FIG. 15B is a section view of the alternate surgical tool module of FIG. 15A.
Figure 15C:
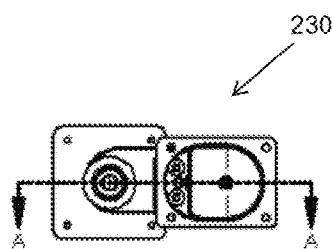
FIG. 15C is a bottom view of the alternate surgical tool module of FIGS. 15A and B.

An alternate embodiment of a surgical tool module 230 is shown in FIG. 15. This embodiment is similar to that shown in FIG. 14 but rather than timing belt and pulleys it uses pneumatic actuators. The surgical tool module 230 includes an ultrasonic motor 232, an encoder 233, a motor plate 234, a timing belt and a pair of pulleys 235, 236, and a pneumatic unit 238. Preferably the ultrasonic motor includes an encoder and more specifically an optical encoder. The surgical tool module 230 is also for use with a drill kit 220. The surgical tool module 230 includes a combined drill support and plate 231 for supporting the drill kit 220. Bearings are included where needed. The ultrasonic motor 232 is operably connected to the timing belt and pulleys 235,236, which in turn are operably connected to the pneumatic unit 238 and the drill kit 220 to rotate the drill. Thereby the ultrasonic motor 232 is also operably connected to pneumatic unit 238. The pneumatic unit 238 is used for driving the trocar locking and retracting mechanism.

The pneumatic actuator 238 is MR compatible. The pneumatic actuator 238 has a piston 237 which is connectable to the drill kit 220. Pulley 235 has a slot that is incorporated with the end of serrated hollow drill 252 of the drill kit 220 for the drill rotating. The guide stylet 254 of the drill kit 220 can be locked with a small air actuator 239. The pneumatic actuator 238 can lock the position of the piston 237 or move the position and thus the position of the drill kit is similarly lockable or moveable. This is actuated pneumatically with compressed air and vacuum. Thus with the use of the pneumatic actuator 238 the movement of the drill kit 220 as described below in reference to FIG. 20 can be achieved. As is well understood by those skilled in the art, in order to provide such control the pneumatic unit 238 may include single or double acting cylinders. The pneumatic cylinders could be actuated with compressed air and/or vacuum. They could operate by simple ON—OFF type control. Because the operating fluid is air, leakage from a pneumatic cylinder will not contaminate the surroundings.

Figure 16:
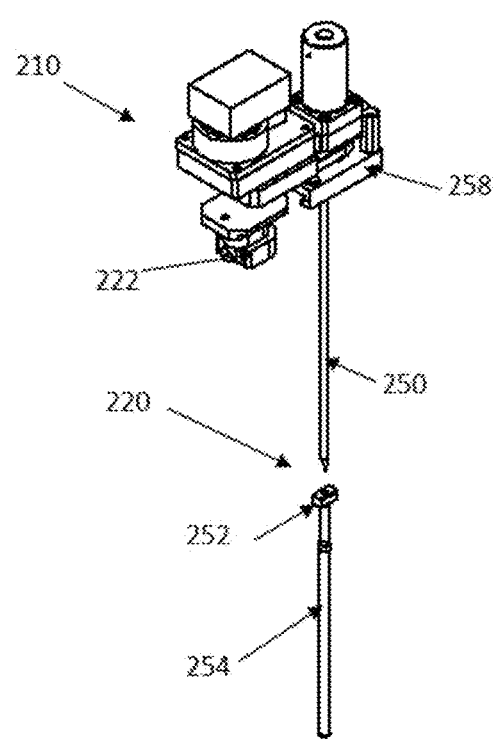
FIG. 16 is a partially exploded perspective view of the surgical tool similar to that shown in FIG. 13 but showing the drill kit in an exploded view.
Figure 17:
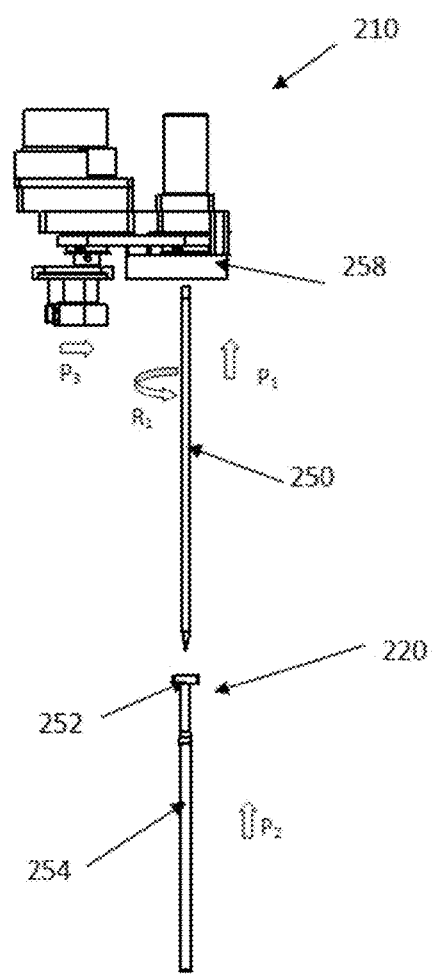
FIG. 17 is a front view of surgical tool of FIG. 16.
Figure 18:
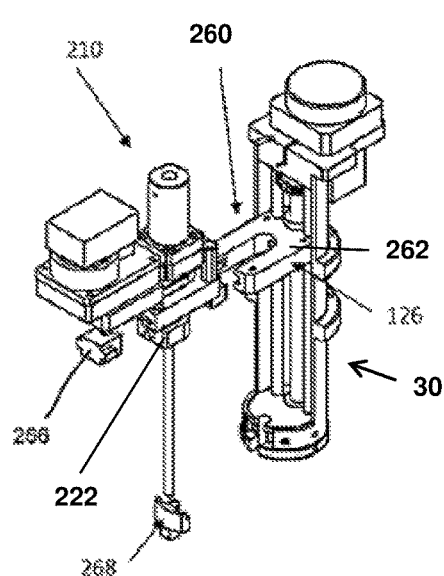
FIG. 18 is an exploded perspective view of surgical tool and the penetration module.
Figure 19:
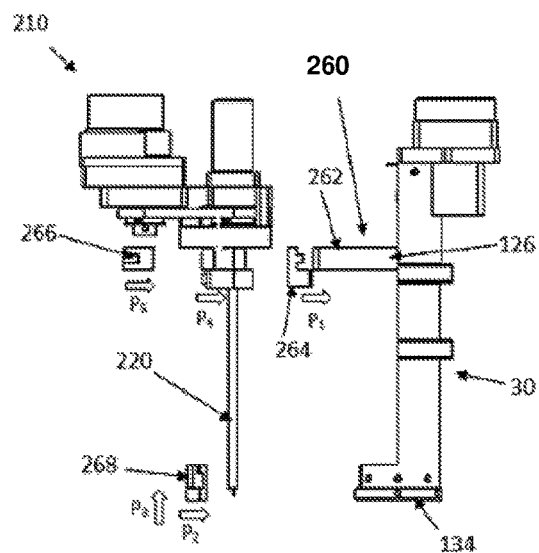
FIG. 19 is a side view of surgical tool and penetration module of FIG. 17.

Referring to FIGS. 16 and 17, preferably the drill kit 220 includes a trocar 250, serrated hollow drill 252 and a guide stylet 254. Referring to FIGS. 18 and 19 the surgical tool 210 is shown with penetration module 30. Penetration module is similar to that shown in FIG. 7 but it includes an alternate adapter 260 as part of nut 126. Adapter 260 includes a nut portion 262, a removable front adapter portion 264 and a removable front closure portion 266. The removable front adapter portion 264 is connectable to the nut portion 262 and the removable front closure portion 266 is connectable to the removable front adapter portion 264. The front adapter portion 264 is for guiding the drill kit 220 of the surgical tool 210, and the front closure portion 266 is for locking the surgical tool 210. In the embodiment shown in FIGS. 18 and 19 a front guiding part 268 is also included for guiding the drill kit 220 while sampling. In use, the drill kit 220 (trocar 250, serrated hollow drill 252 and guide stylet 254), removable front adapter portion 264, removable drill support 222, removable front closure portion and removable front guiding part 268 are sterilized prior to use. Then each item is installed or re-installed in their respective module. Preferably the range of motion of the trocar retracting stroke is 0-25 mm.

Referring to FIG. 17, following is the procedure for inserting the drill kit into the surgical tool module of FIG. 14:

1. Insert ($P_1$) trocar 250 with end thread into surgical tool module 210 and rotate it ($R_1$) a few turns;

2. Insert serrated hollow drill 252 into guide stylet 254, and push ($P_2$) them into the surgical tool module 210; and
3. Push ($P_3$) drill support 222 into the slot plate 258

Once the surgical tool 210 is assembled or reassembled after sterilizing certain element it is then inserted in to the penetration module 30 as shown in FIG. 19 and as described following:

1. Push ($P_1$) front adapter portion 264 into the adapter nut portion 262;
2. Slide front guiding part 268 to stylet 254 of drill kit 220 ($P_2$ and $P_3$);
3. Push ($P_4$) surgical tool 210 with front guiding part 268 into penetration module 30 (adapter 260 and front support part 134); and
4. Push ($P_5$) closure 266 into the adapter 260.

Figure 20:
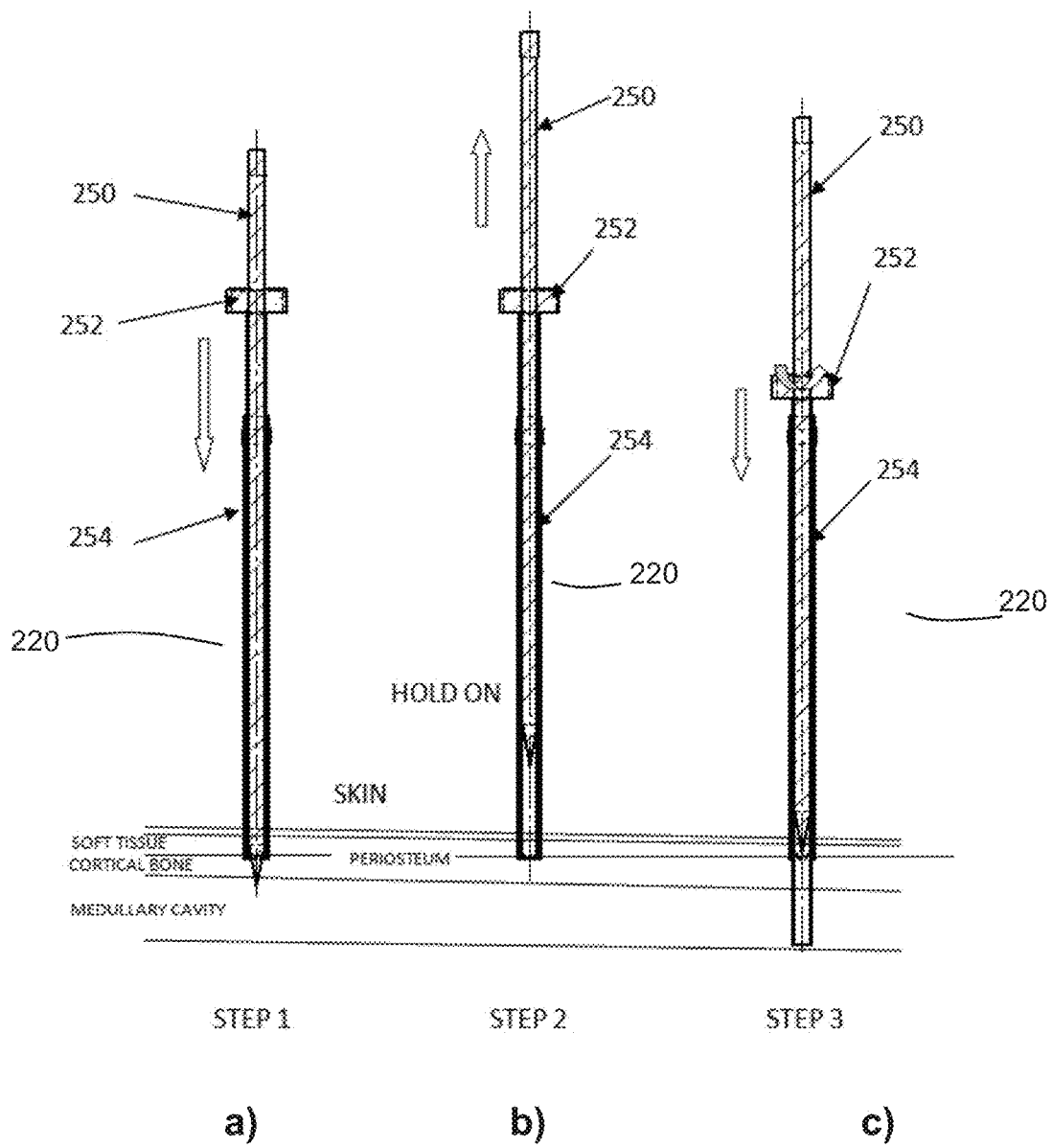
FIG. 20 is a perspective view of the biopsy procedure with a 3-piece drill kit with a) being step 1, b) step 2 and c) step 3.

The surgical tool 210 described above is particularly useful for automatic sampling. The protocol for automatic sampling is similar to the current manual procedure. Referring to FIG. 20, the drill kit 220 may be known as a bone biopsy tooling manifold. As described above, the drill kit 220 includes a trocar 250, a sterile serrated hollow drill 252 and a stationary (outer) sheath or guide stylet 254. The stationary (outer) sheath or guide stylet 254 would allow the serrated hollow drill to continue to spin while the centre needle is used to make the puncture. The protocol is as follows:

1. Penetrating (without rotating) the trocar 250, serrated hollow drill 252 and guide stylet 254 to cortical bone (linear motions). The pointed trocar 250 is inserted into the serrated hollow drill 252, and they are inserted into guide stylet 254, and then inserted into the incision until the trocar tip comes in contact with the bone. The tip of the trocar could be moved from side to side to free adhering structures from the bony surface. The drill kit is then pushed until guide stylet 254 rests firmly on the bony surface (FIG. 20 (*a*)).
2. Holding the guide style 254 in place, then retracting the trocar 250 back about 20 mm or more (linear motion) (FIG. 20 (*b*)).
3. Holding the guide stylet 254 in place, advancing (by rotating) the serrated hollow drill 252 to the target for sampling (linear and rotary motions) (FIG. 20 (*c*)).
4. Once the serrated hollow drill has been felt to pass completely through the bone, the pushing is stopped, and the serrated hollow drill is rotated through two complete revolutions. This step would ensure that the medial surface of the specimen is free from its periosteal attachments.
5. Then pull back out the drill kit (not shown) such that the drill kit is pulled out of the bone and skin.

Figure 21:
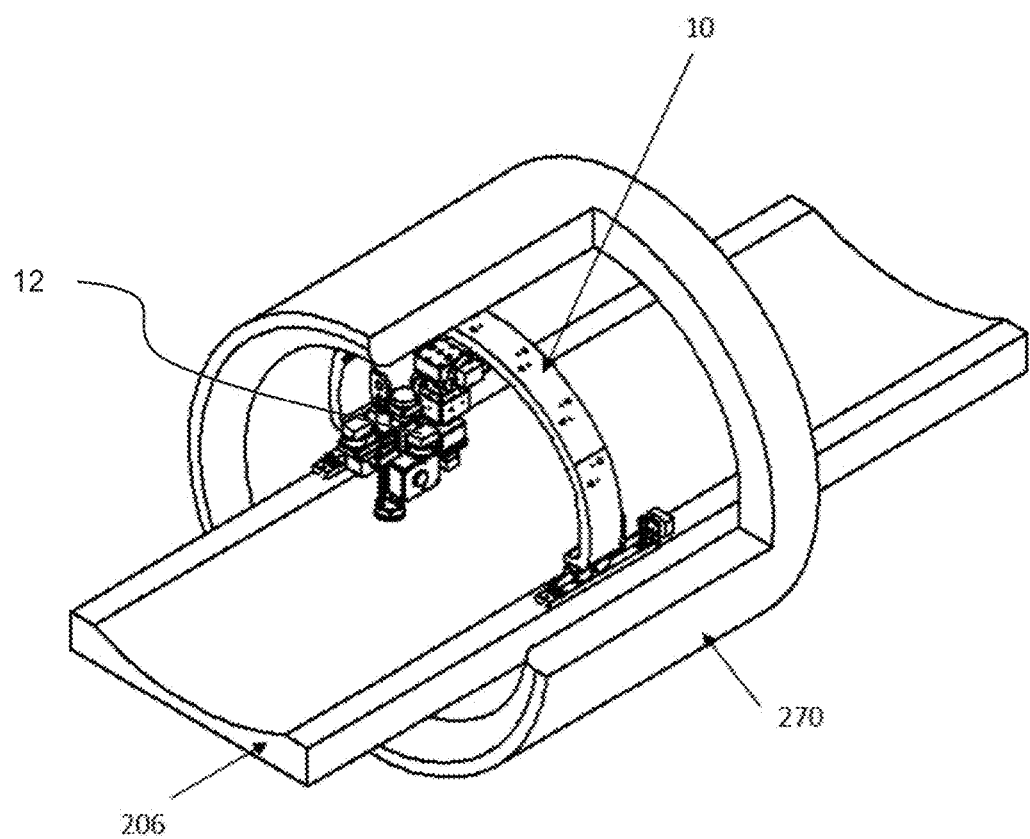
FIG. 21 is a perspective view of the surgical robot assembly of FIG. 1 shown in an MRI and showing a portion of the MRI broken away.
Figure 22:
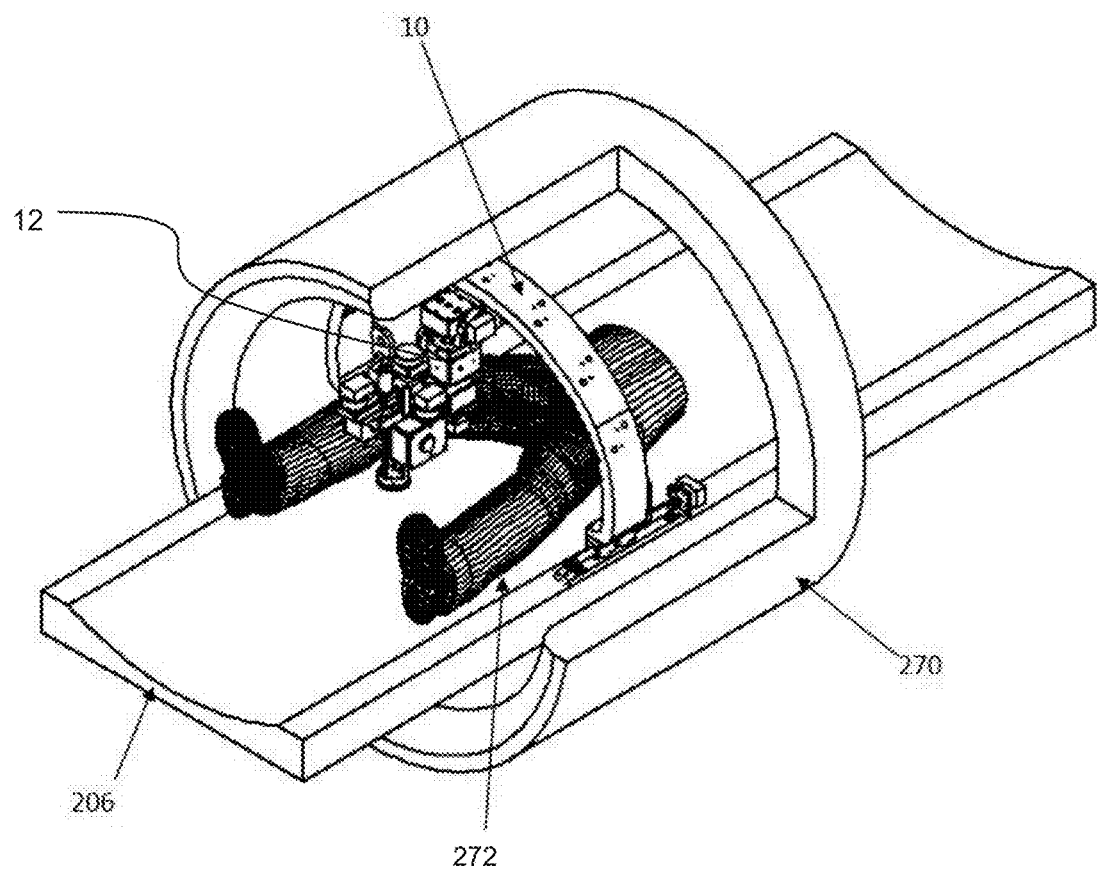
FIG. 22 is a perspective view of the surgical robot assembly similar to that shown in FIG. 21 but also showing the legs of a patient.

Referring to FIGS. 21 and 22 the surgical robot assembly 10 is shown in situ in an MRI 270. The surgical robot assembly 10 is shown attached to an MRI table 206. By way of example in FIG. 22 the surgical robot assembly is shown how it may be positioned around the legs of a person 272.

Figure 23:
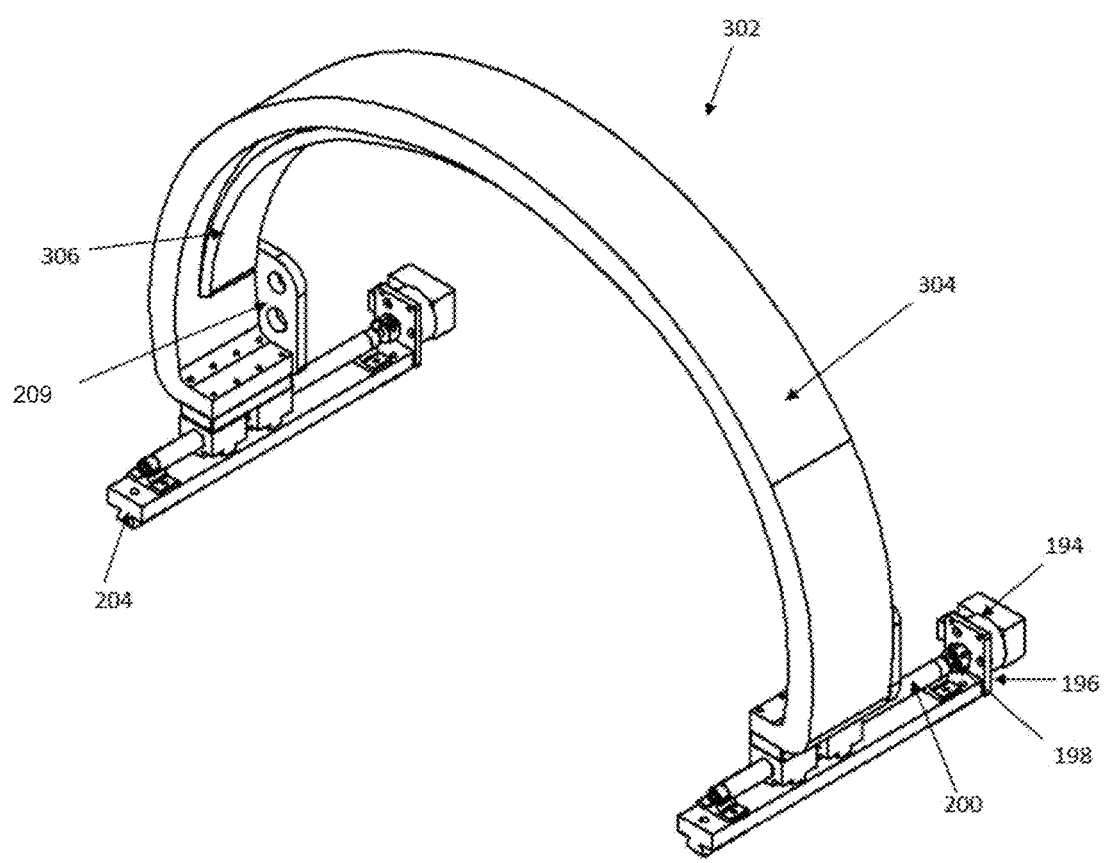
FIG. 23 is a perspective view of an alternate arch device similar to that shown in FIG. 13 but including an arch guide rail module.
Figure 24A:
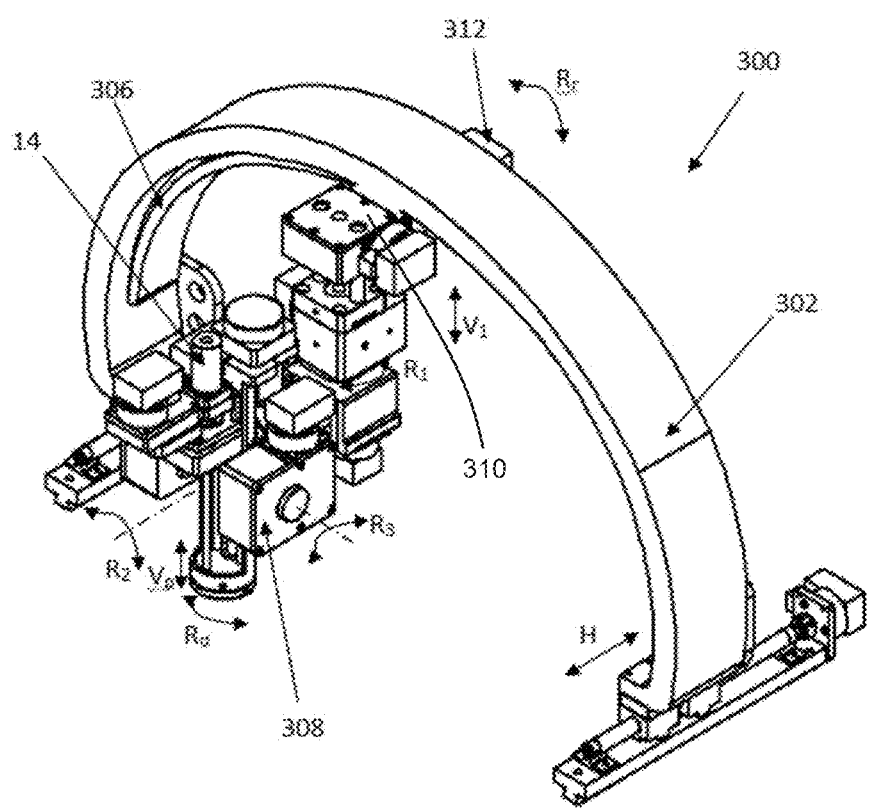
FIG. 24A is a perspective view of an alternate embodiment of a surgical robot assembly that is similar to that shown in FIG. 1 but including the arch device of FIG. 23 and a robot rotary module for moving the surgical robot along the arch device.
Figure 24B:
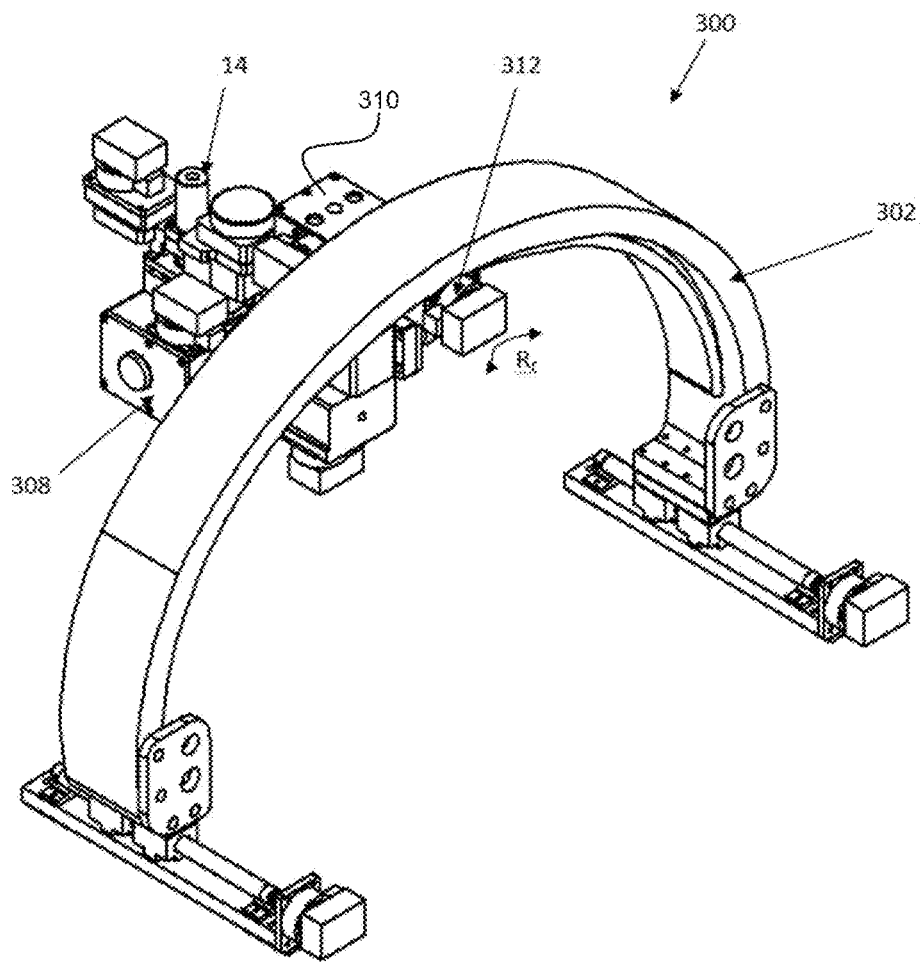
FIG. 24B is a perspective view of the alternate embodiment of a surgical robot assembly of FIG. 24A but viewed from another direction.
Figure 25:
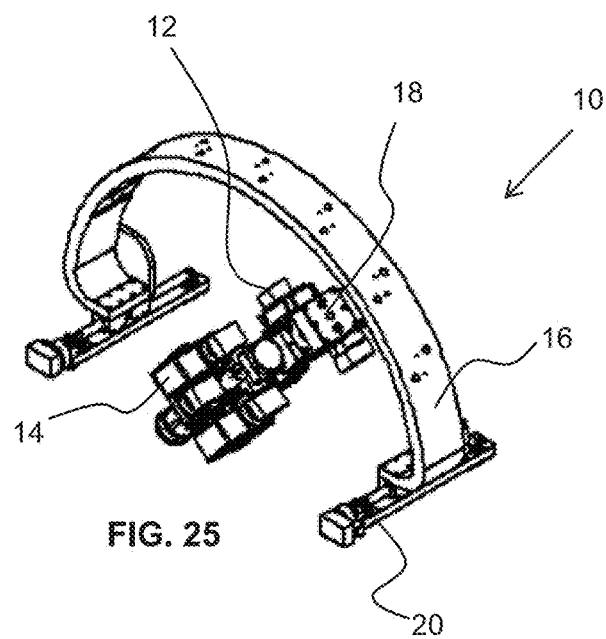
FIG. 25 is a perspective view of the surgical robot assembly of FIG. 1 but showing the surgical robot attached at an alternate location along the arch device.
Figure 26:
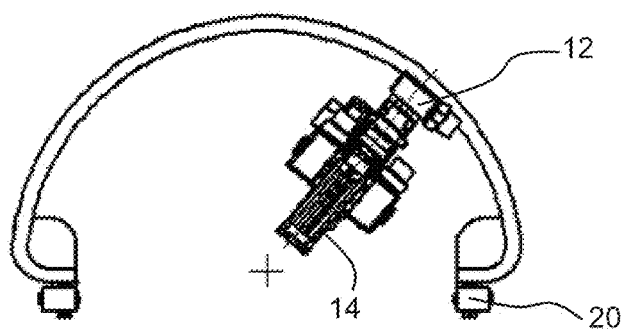
FIG. 26 is a front view of the surgical robot assembly of FIG. 25.

An alternate embodiment of the surgical robot assembly 300 is shown in FIGS. 24A and 24B. Surgical robot assembly 300 is similar to surgical robot assembly 10 but it includes an alternate arch device unit 302 shown in FIG. 23. Arch device unit 302 includes an arch frame 304 with a rail 306 fixedly mounted on the inner side of the arch frame 304. The remainder of the arch device unit 302 is the same as described above with regard to arch unit 16. The surgical robot 308 is similar to that described above except that its attachment device 310 is adapted to engage rail 306. Surgical robot 308 can be movably attached to the rail 306 of the arch device unit 302 through a mounting mechanism 310 that is a part of the Quick/Simple Connect Attachment.

Once the surgical robot 308 is attached to the rail 306 its trajectory is constrained by the rail. The robot can move along the rail to any position, either manually or driven by an arch ultrasonic motor unit 312. Preferably ultrasonic motor unit 312, includes a USR™ ultrasonic motor with encoder and a gear mechanism. Ultrasonic motor unit 312 is part of attachment device 310 and operably attached to surgical robot 308. The attachment device 310 engages the rail 306 and thus surgical robot 308 can move along the arch device unit 302.

When the robot reaches a defined position on the rail, it can be locked onto it by a locking mechanism. The position of the robot on the rail can be measured by sensors. The measurement is fed to the robot system for registration and kinematics calculations.

Figure 27A:
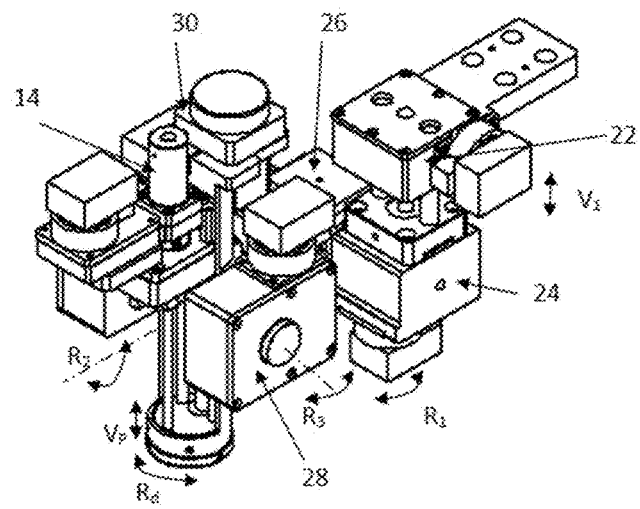
FIG. 27A is a perspective view of the surgical robot of FIG. 2A but showing the modules configured differently.
Figure 27B:
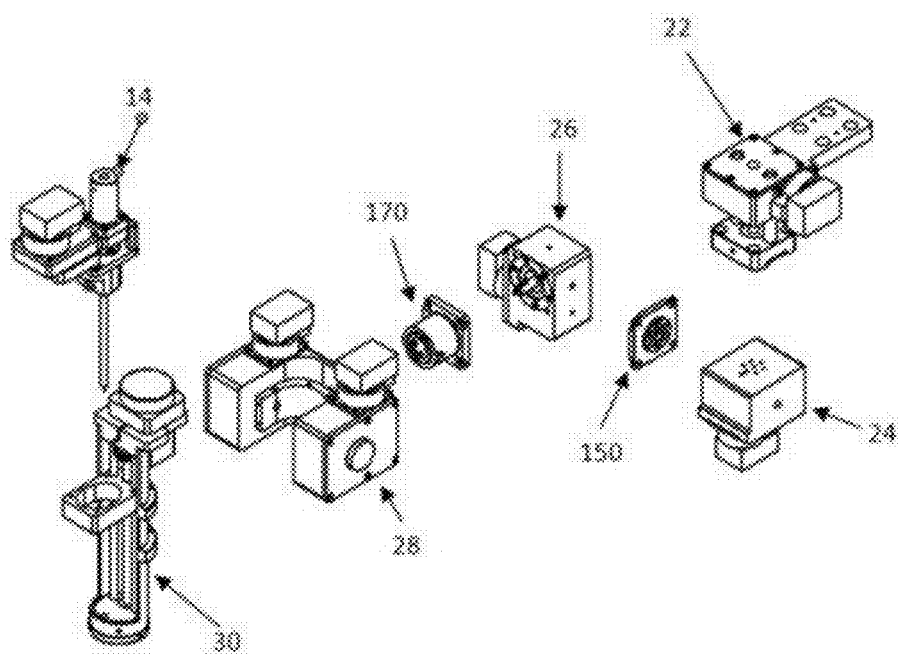
FIG. 27B is a blown apart perspective view of the surgical robot of FIG. 27A.

It will be appreciated by those skilled in the art that the surgical robot 12 is a modular reconfigurable robot and can be reconfigured to suit different types of surgery, as shown in FIGS. 27 and 28. In the embodiment shown in FIGS. 27A and 27B, linear module 22 is connected to turret module 24, which is connected to elbow roll module 26, a wrist tilt module 28, a penetration module 30 and a surgical tool module 14. The turret module 24 and the elbow roll module 26 are connected with a turret and elbow connection unit 150. The elbow roll module 26 and the wrist tilt module 28 are connected with the roll connection unit 170. The orientation of turret module 24 and elbow roll module 26 is different than that shown in FIGS. 1 to 26 so that the surgical robot may be used for a different application.

Figure 28A:
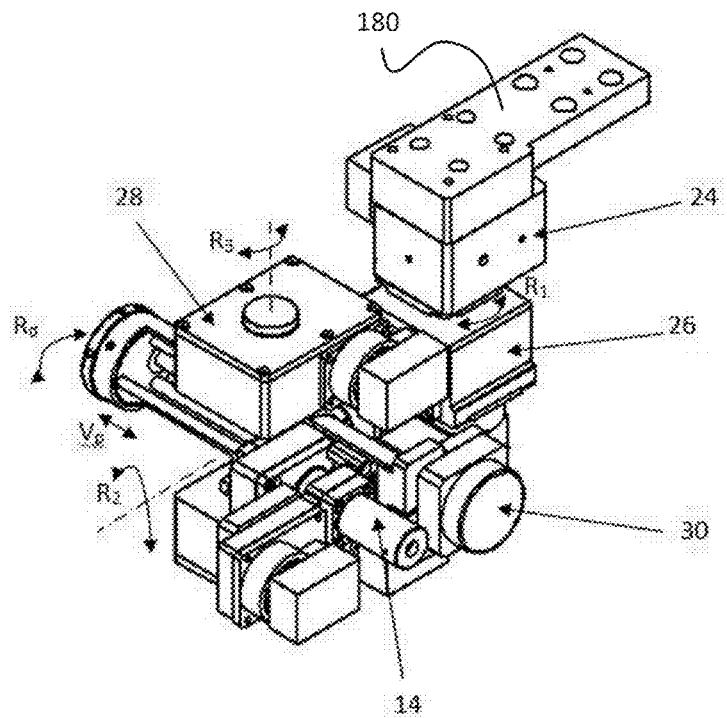
FIG. 28A is a perspective view of the surgical robot of FIG. 2A but showing the modules configured differently from FIG. 2A and FIG. 27A.
Figure 28B:
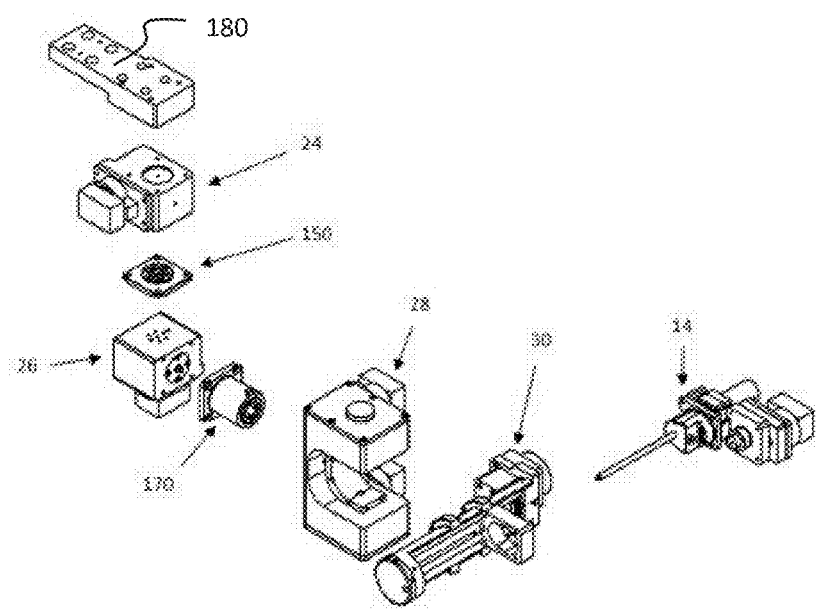
FIG. 28B is a blown apart perspective view of the surgical robot of FIG. 28A.

Similarly, in the embodiment shown in FIGS. 28A and 28B, turret module 24 is connected to elbow roll module 26, a wrist tilt module 28, a penetration module 30 and a surgical tool module 14. In addition a quick connector 180 may be provided. Quick connector module 180 is attached to the turret module 24. The turret module 24 and the elbow roll module 26 are connected with a turret and elbow connection unit 150. The elbow roll module 26 and the wrist tilt module 28 are connected with the roll connection unit 170. The orientation of wrist tilt module 28 is different than that shown in FIGS. 1 to 26 and 27 so that the surgical robot may be used for a different application. In addition the orientation of the surgical tool module 14 is different and is generally horizontal in this configuration.

It will be appreciated by those skilled in the art that the modules of the surgical robot described herein may be modified. For example the main modules such as the linear module, the turret module, the elbow wrist tilt module, may be modified to include connection features such that the module can then be connected directly to another module. An example of this is shown in FIG. 30 wherein the elbow roll module 500 and the wrist tilt module 400 each include connection features.

It will be appreciated by those skilled in the art that the surgical robot may have a plurality of coordinate systems that are relevant to the operation thereof. For example the surgical robot assembly 10 has an inertial or fixed frame coordinate system 11 as shown in FIG. 1. This coordinate system has a z axis in the direction of travel of the pair of rails 20 of the arch unit 16. In addition there may be a surgical robot 12 coordinate system 13 as shown in FIG. 2 wherein the linear module defines a z axis: the turret module has rotational movement in an axis parallel to the z axis; the elbow roll module has rotational movement around an x axis and the x axis is generally orthogonal to the z axis; and the wrist tilt module has rotational movement around a y axis and the y axis is generally orthogonal to the z axis and transverse to the x axis. It will be appreciated by those skilled in the art that the inertial frame coordinate system 11 is fixed while the surgical robot coordinate system travels as the robot travels.

In general, the systems described herein are directed to medical robots for use in an MRI. Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

What is claimed is:

1. A modular reconfigurable surgical robot for use in an MRI and for use in association with a surgical tool comprising:
a linear module for linear movement having a linear movement axis;
a turret module for rotational movement having a turret rotational axis;
an elbow roll module for rotational movement having an elbow roll rotational axis being at an angle to the turret rotational axis;
a wrist tilt module for rotational movement having a wrist tilt rotational axis being at an angle to the turret rotational axis and being at an angle to the elbow roll rotational axis;
wherein the linear module, turret module, elbow roll module and wrist tilt module are operably connectable together to form the surgical robot and one of the turret module, elbow roll module and wrist tilt module is operably connectable to the surgical tool;
wherein the linear module moves the module operably connectable to the surgical tool parallel to the linear movement axis of the linear module; and
wherein the modules of the surgical robot are re-configurable in a plurality of different configurations such that the surgical robot fits within an MRI.

2. The modular reconfigurable surgical robot of claim 1 wherein the linear movement of the linear module defines a z axis, the turret rotational axis is an axis parallel to the z axis; the elbow roll rotational axis is around an x axis and the x axis is generally orthogonal to the z axis; and the wrist tilt rotational axis is around a y axis and the y axis is generally orthogonal to the z axis and transverse to the x axis.

3. The modular reconfigurable surgical robot of claim 1 further including a penetration module connectable to the surgical robot and the surgical tool is attachable to the penetration module.

4. The modular reconfigurable surgical robot of claim 3 further including a turret elbow connection module connectable to the turret module and the elbow roll module.

5. The modular reconfigurable surgical robot of claim 4 further including a roll connection unit connectable to the wrist tilt module and the elbow roll module.

6. The modular reconfigurable surgical robot of claim 3 wherein the penetration module includes a lead screw, a nut, and a gear mechanism, the gear mechanism being operably connected to a motor.

7. The modular reconfigurable surgical robot of claim 6 wherein the gear mechanism of the penetration module includes a pair of spur gears and the motor of the penetration module is an ultrasonic rotary motor.

8. The modular reconfigurable surgical robot of claim 3 wherein the surgical tool is a surgical tool module connectable to the penetration module and the surgical tool module includes a lead screw, a nut, and a gear mechanism, the gear mechanism being operably connected to a motor of the surgical tool module.

9. The modular reconfigurable surgical robot of claim 8 wherein the surgical tool module is operably connectable to a drill kit.

10. The modular reconfigurable surgical robot of claim 9 wherein the surgical tool module further includes a timing belt and pulleys operably connectable to the drill kit.

11. The modular reconfigurable surgical robot of claim 9 wherein the surgical tool module includes a pneumatic unit operably connectable to the drill kit.

12. The modular reconfigurable surgical robot of claim 9 wherein the drill kit includes a trocar, a drill, and a guide stylet.

13. The modular reconfigurable surgical robot of claim 9 wherein the penetration module further includes an adapter and the surgical tool module is attachable to the adapter.

14. The modular reconfigurable surgical robot of claim 13 wherein the adapter includes a nut portion, a removable front adapter portion connectable to the nut portion and a removable front closure portion connectable to the removable front adapter portion.

15. The modular reconfigurable surgical robot of claim 14 wherein the surgical tool module includes a removable support releasably connectable to a slot plate.

16. The modular reconfigurable surgical robot of claim 15 wherein the removable front adapter portion, the removable front closure portion, the removable support and the drill kit are all sterilizable using existing medical sterilization systems.

17. The modular reconfigurable surgical robot of claim 8 wherein the motor of the surgical tool module is an ultrasonic rotary motor.

18. The modular reconfigurable surgical robot of claim 1 wherein the linear module includes a lead screw, a nut, and a gear mechanism, the gear mechanism being operably connected to a motor.

19. The modular reconfigurable surgical robot of claim 18 wherein the gear mechanism of the linear module includes a worm and a worm gear and the motor is an ultrasonic rotary motor.

20. The modular reconfigurable surgical robot of claim 19 wherein the linear module includes a hard stop to limit movement of the nut.

21. The modular reconfigurable surgical robot of claim 1 wherein the turret module includes a shaft and a gear mechanism operably connected to a motor.

22. The modular reconfigurable surgical robot of claim 21 wherein the gear mechanism of the turret module includes a worm and a worn gear and the motor of the turret module is an ultrasonic rotary motor.

23. The modular reconfigurable surgical robot of claim 22 wherein the turret module includes a hard stop to limit the rotation of the shaft.

24. The modular reconfigurable surgical robot of claim 1 wherein the elbow roll module includes a shaft and a gear mechanism operably connected to a motor.

25. The modular reconfigurable surgical robot of claim 24 wherein the gear mechanism of the elbow roll module includes a worm and a worm gear and the motor of the elbow roll module is an ultrasonic rotary motor.

26. The modular reconfigurable surgical robot of claim 25 wherein the elbow roll module includes a hard stop to limit the rotation of the shaft.

27. The modular reconfigurable surgical robot of claim 1 wherein the wrist tilt module includes a pair of shafts and a pair of gear mechanism operably connected to a pair of motor.

28. The modular reconfigurable surgical robot of claim 27 wherein each gear mechanism of the wrist tilt module includes a worm and a worm gear and the motor of the wrist tilt module is an ultrasonic rotary motor.

29. The modular reconfigurable surgical robot of claim 28 wherein the wrist tilt module includes a hard stop to limit the rotation of the shaft.

30. The modular reconfigurable surgical robot of claim 1 further including an arch device unit operably attachable to one of the linear module, the turret module, the elbow roll module and the wrist tilt module.

31. The modular reconfigurable surgical robot of claim 30 wherein the arch device unit further includes a pair of linear actuators at either end of an arch frame.

32. The modular reconfigurable surgical robot of claim 31 wherein each linear actuator of the arch device unit includes an ultrasonic motor operably connected to a lead screw and a pair of carriages moveably connected to the lead screw and whereby the pair of carriages is connected to the arch frame and activating the ultrasonic motor moves the carriage along the lead screw.

33. The modular reconfigurable surgical robot of claim 32 wherein each linear actuator is connected to a base plate and the base plate is connectable to a surgical table.

34. The modular reconfigurable surgical robot of claim 30 further including a quick connector module connectable to one of the linear module, the turret module, the elbow roll module and the wrist tilt module.

35. The modular reconfigurable surgical robot of claim 30 wherein the arch device unit includes a rail and the surgical robot is movably attached to the rail.

36. The modular reconfigurable surgical robot of claim 35 wherein the surgical robot is moved manually along the rail.

37. The modular reconfigurable surgical robot of claim 35 wherein the arch device unit further includes an arch motor to driven surgical robot along the rail.

38. The modular reconfigurable surgical robot of claim 1 wherein all of the elements of the modular reconfigurable surgical robot are MRI compatible.

* * * * *